(12) United States Patent
Weiss

(10) Patent No.: US 10,822,386 B2
(45) Date of Patent: Nov. 3, 2020

(54) INSULIN ANALOGUES WITH ENHANCED STABILITY AND REDUCED MITOGENICITY

(71) Applicant: CASE WESTERN RESERVE UNIVERSITY, Cleveland, OH (US)

(72) Inventor: Michael Weiss, Moreland Hills, OH (US)

(73) Assignee: Case Western Reserve University, Cleveland, OH (US)

( * ) Notice: Subject to any disclaimer, the term of this patent is extended or adjusted under 35 U.S.C. 154(b) by 251 days.

(21) Appl. No.: 15/539,450

(22) PCT Filed: Dec. 24, 2015

(86) PCT No.: PCT/US2015/000365
§ 371 (c)(1),
(2) Date: Jun. 23, 2017

(87) PCT Pub. No.: WO2016/105545
PCT Pub. Date: Jun. 30, 2016

(65) Prior Publication Data
US 2020/0140516 A1 May 7, 2020

Related U.S. Application Data

(60) Provisional application No. 62/096,776, filed on Dec. 24, 2014.

(51) Int. Cl.
*C07K 14/62* (2006.01)
*A61K 38/00* (2006.01)

(52) U.S. Cl.
CPC .............. *C07K 14/62* (2013.01); *A61K 38/00* (2013.01)

(58) Field of Classification Search
CPC .................. C07K 14/62; A61K 38/00
See application file for complete search history.

(56) References Cited

U.S. PATENT DOCUMENTS

| 9,200,053 | B2* | 12/2015 | Weiss | C07K 14/62 |
| 9,725,493 | B2* | 8/2017 | Weiss | C07K 14/62 |
| 9,901,622 | B2* | 2/2018 | Joseph | A61K 36/05 |
| 9,908,925 | B2* | 3/2018 | Weiss | C07K 14/62 |
| 10,138,284 | B2* | 11/2018 | Weiss | A61P 3/08 |
| 10,472,406 | B2* | 11/2019 | Weiss | C07K 14/62 |
| 10,703,792 | B2* | 7/2020 | Weiss | C07K 14/62 |
| 2014/0235537 | A1* | 8/2014 | Meehl | A61K 38/28 514/6.2 |

FOREIGN PATENT DOCUMENTS

| WO | WO 2013/010048 | * | 1/2013 | C07K 14/62 |
| WO | WO 2013/110069 | * | 7/2013 | A61K 38/28 |

* cited by examiner

*Primary Examiner* — Amber D Steele
(74) *Attorney, Agent, or Firm* — Hahn Loeser & Parks, LLP; John J. Cunniff

(57) ABSTRACT

A polypeptide comprises an insulin B-chain sequence having the substitutions: Asp at position B10, Ala at position B12, and Glu at position B29, relative to wild type insulin. The polypeptide may additionally comprise a substitution of a halogenated phenylalanine at position B24, such as ortho-fluoro-phenylalanine. Optionally, the polypeptide may additionally comprise a C-terminal dipeptide extension wherein at least one amino acid in the dipeptide contains an acidic side chain, such as Glu-Glu, and/or an N-terminal deletion of one, two or three residues from the B chain. An insulin analogue may comprise any of these polypeptides with an insulin A-chain polypeptide that optionally contains a Glu A8 substitution. The A-chain sequence may be a separate polypeptide or it may be joined to the B-chain polypeptide by a two amino acid linker. The linker may be Trp-Lys or Ala-Lys. The insulin analogue may be used to treat a patient with diabetes mellitus.

18 Claims, 8 Drawing Sheets

Specification includes a Sequence Listing.

PROINSULIN

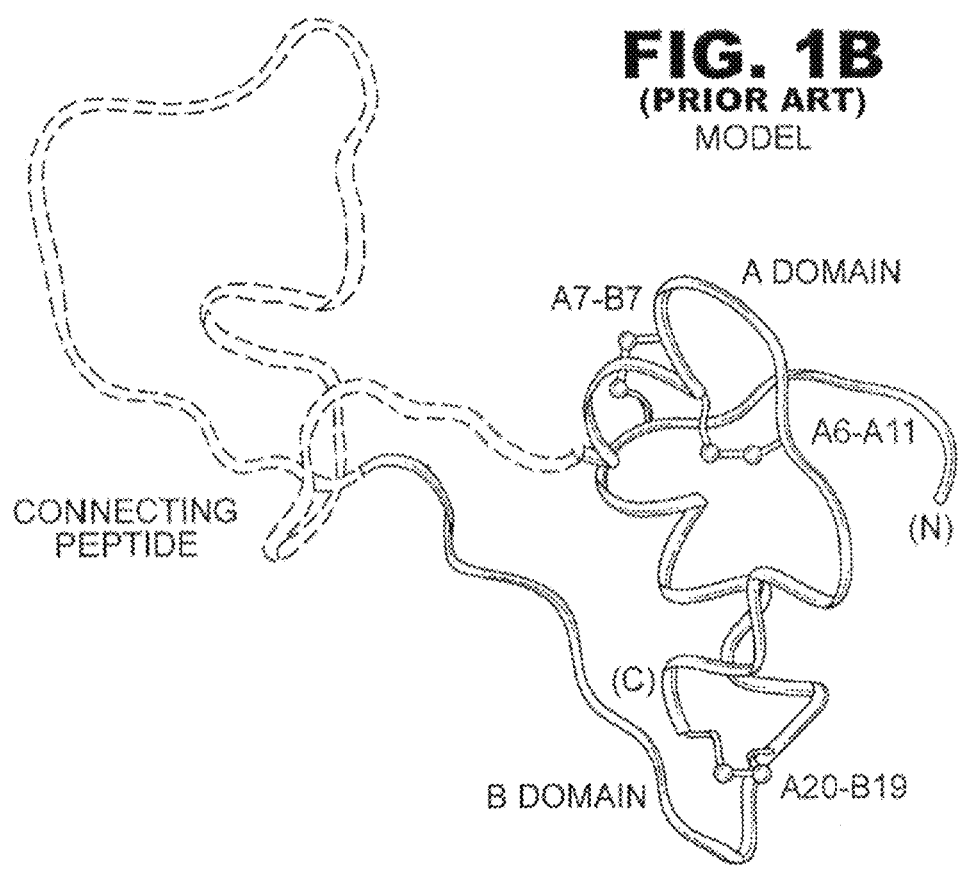

SEQUENCE LISTING

<160> NUMBER OF SEQ ID NOS: 62

<210> SEQ ID NO 1
<211> LENGTH: 86
<212> TYPE: PRT
<213> ORGANISM: Homo sapiens

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 2
<211> LENGTH: 21
<212> TYPE: PRT
<213> ORGANISM: Homo sapiens

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 3
<211> LENGTH: 30
<212> TYPE: PRT
<213> ORGANISM: Homo sapiens

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 4
<211> LENGTH: 21
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is any amino acid other than Val, Leu or
      Ile
<220> FEATURE:
<221> NAME/KEY: MISC_FEATURE
<222> LOCATION: (13)..(13)
<223> OTHER INFORMATION: Xaa is Leu, Trp or Tyr
<220> FEATURE:
<221> NAME/KEY: MISC_FEATURE
<222> LOCATION: (14)..(14)
<223> OTHER INFORMATION: Xaa is Tyr or Glu
<220> FEATURE:
<221> NAME/KEY: MISC_FEATURE
<222> LOCATION: (21)..(21)
<223> OTHER INFORMATION: Xaa is Asn, Asp, Ala or Gly

```
<400> SEQUENCE: 4

Gly Ile Val Glu Gln Cys Cys Xaa Ser Ile Cys Ser Xaa Xaa Gln Leu
1               5                   10                  15

Glu Asn Tyr Cys Xaa
            20

<210> SEQ ID NO 5
<211> LENGTH: 32
<212> TYPE: PRT
<213> ORGANISM: Homo sapiens
<220> FEATURE:
<221> NAME/KEY: MISC_FEATURE
<222> LOCATION: (1)..(3)
<223> OTHER INFORMATION: Xaa is Phe-Val-Asn, Val-Asn,  Asn or 0 amino
      acids
<220> FEATURE:
<221> NAME/KEY: MISC_FEATURE
<222> LOCATION: (24)..(24)
<223> OTHER INFORMATION: Xaa is Phe or a halogenated Phenylalanine
<220> FEATURE:
<221> NAME/KEY: MISC_FEATURE
<222> LOCATION: (28)..(28)
<223> OTHER INFORMATION: Xaa is Pro, Lys, Ala, or Gln
<220> FEATURE:
<221> NAME/KEY: MISC_FEATURE
<222> LOCATION: (31)..(32)
<223> OTHER INFORMATION: Xaa is 0-2 amino acids wherein at least one
      amino acid residue is Glu or Asp, if present

<400> SEQUENCE: 5

Xaa Xaa Xaa Gln His Leu Cys Gly Ser Asp Leu Ala Glu Ala Leu Tyr
1               5                   10                  15

Leu Val Cys Gly Glu Arg Gly Xaa Phe Tyr Thr Xaa Glu Thr Xaa Xaa
            20                  25                  30

<210> SEQ ID NO 6
<211> LENGTH: 30
<212> TYPE: PRT
<213> ORGANISM: Homo sapiens

<400> SEQUENCE: 6

Phe Val Asn Gln His Leu Cys Gly Ser Asp Leu Ala Glu Ala Leu Tyr
1               5                   10                  15

Leu Val Cys Gly Glu Arg Gly Phe Phe Tyr Thr Pro Glu Thr
            20                  25                  30

<210> SEQ ID NO 7
<211> LENGTH: 21
<212> TYPE: PRT
<213> ORGANISM: Homo sapiens

<400> SEQUENCE: 7

Gly Ile Val Glu Gln Cys Cys Glu Ser Ile Cys Ser Leu Tyr Gln Leu
1               5                   10                  15

Glu Asn Tyr Cys Asn
            20

<210> SEQ ID NO 8
<211> LENGTH: 32
<212> TYPE: PRT
<213> ORGANISM: Homo sapiens

<400> SEQUENCE: 8

Phe Val Asn Gln His Leu Cys Gly Ser Asp Leu Ala Glu Ala Leu Tyr
1               5                   10                  15
```

Leu Val Cys Gly Glu Arg Gly Phe Phe Tyr Thr Pro Glu Thr Glu Glu
            20                  25                  30

<210> SEQ ID NO 9
<211> LENGTH: 30
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: Xaa is ortho fluoro Phe

<400> SEQUENCE: 9

Phe Val Asn Gln His Leu Cys Gly Ser Asp Leu Ala Glu Ala Leu Tyr
1               5                   10                  15

Leu Val Cys Gly Glu Arg Gly Xaa Phe Tyr Thr Pro Glu Thr
            20                  25                  30

<210> SEQ ID NO 10
<211> LENGTH: 30
<212> TYPE: PRT
<213> ORGANISM: Homo sapiens
<220> FEATURE:
<221> NAME/KEY: MISC_FEATURE
<222> LOCATION: (1)..(3)
<223> OTHER INFORMATION: Xaa is Phe-Val-Asn, Val-Asn, Asn or 0 amino
      acids

<400> SEQUENCE: 10

Xaa Xaa Xaa Gln His Leu Cys Gly Ser Asp Leu Ala Glu Ala Leu Tyr
1               5                   10                  15

Leu Val Cys Gly Glu Arg Gly Phe Phe Tyr Thr Pro Glu Thr
            20                  25                  30

<210> SEQ ID NO 11
<211> LENGTH: 32
<212> TYPE: PRT
<213> ORGANISM: Homo sapiens
<220> FEATURE:
<221> NAME/KEY: MISC_FEATURE
<222> LOCATION: (1)..(3)
<223> OTHER INFORMATION: Xaa is Phe-Val-Asn, Val-Asn, Asn or 0 amino
      acids

<400> SEQUENCE: 11

Xaa Xaa Xaa Gln His Leu Cys Gly Ser Asp Leu Ala Glu Ala Leu Tyr
1               5                   10                  15

Leu Val Cys Gly Glu Arg Gly Phe Phe Tyr Thr Pro Glu Thr Glu Glu
            20                  25                  30

<210> SEQ ID NO 12
<211> LENGTH: 30
<212> TYPE: PRT
<213> ORGANISM: Homo sapiens
<220> FEATURE:
<221> NAME/KEY: MISC_FEATURE
<222> LOCATION: (1)..(3)
<223> OTHER INFORMATION: Xaa is Phe-Val-Asn, Val-Asn, Asn or 0 amino
      acids
<220> FEATURE:
<221> NAME/KEY: MISC_FEATURE
<222> LOCATION: (24)..(24)
<223> OTHER INFORMATION: Xaa is ortho fluoro Phe

<400> SEQUENCE: 12

Xaa Xaa Xaa Gln His Leu Cys Gly Ser Asp Leu Ala Glu Ala Leu Tyr
1               5                   10                  15

Leu Val Cys Gly Glu Arg Gly Xaa Phe Tyr Thr Pro Glu Thr
            20                  25                  30

<210> SEQ ID NO 13
<211> LENGTH: 162
<212> TYPE: DNA
<213> ORGANISM: Homo sapiens

<400> SEQUENCE: 13
ttcgtcaatc aacacttgtg tggtagtgac ttggcagagg cattgtactt ggtctgtggt     60
gagagaggat tcttctacac cccaaaggag tggaagggta tcgttgagca atgttgtact    120
tccatctgct cattgtacca attggagaac tactgcaact aa                      162

<210> SEQ ID NO 14
<211> LENGTH: 162
<212> TYPE: DNA
<213> ORGANISM: Homo sapiens

<400> SEQUENCE: 14
ttcgtcaatc aacacttgtg tggtagtgac ttggcagagg ctttgtactt ggtctgtggt     60
gagagaggat tcttctacac ccctaaggct gctaagggaa tcgttgagca atgctgtact    120
tccatctgct cattgtacca attggagaac tactgcaact aa                      162

<210> SEQ ID NO 15
<211> LENGTH: 162
<212> TYPE: DNA
<213> ORGANISM: Homo sapiens

<400> SEQUENCE: 15
ttcgtcaatc aacacttgtg tggtagtgac ttggcagagg cattgtactt ggtctgtggt     60
gagagaggat tcttctacac cccaaaggag tggaagggta tcgttgagca atgttgtgaa    120
tccatctgct cattgtacca attggagaac tactgcaact aa                      162

<210> SEQ ID NO 16
<211> LENGTH: 171
<212> TYPE: DNA
<213> ORGANISM: Homo sapiens

<400> SEQUENCE: 16
ttcgtcaatc aacacttgtg tggtagtgac ttggcagagg cattgtactt ggtctgtggt     60
gagagaggat agttctacac cccaaaggag tggaagggta tcgttgagca atgttgtact    120
tccatctgct cattgtacca attggagaac tactgcaact aatagttcta c             171

<210> SEQ ID NO 17
<211> LENGTH: 162
<212> TYPE: DNA
<213> ORGANISM: Homo sapiens

<400> SEQUENCE: 17
ttcgtcaatc aacacttgtg tggtagtgac ttggcagagg cattgtactt ggtctgtggt     60
gagagaggat agttctacac cccaaaggag tggaagggta tcgttgagca atgttgtgaa    120
tccatctgct cattgtacca attggagaac tactgcaact aa                      162

<210> SEQ ID NO 18
<211> LENGTH: 162
<212> TYPE: DNA
<213> ORGANISM: Homo sapiens
<220> FEATURE:

```
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 18
ttcgtcaatc aacacttgtg tggtagtgac ttggcagagg cattgtactt ggtctgtggt      60
gagagaggat tcttctacac cccaaaggag tggaagggta tcgttgagca atgttgtact     120
tccatctgct cannnnnnca attggagaac tactgcaact aa                        162

<210> SEQ ID NO 19
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 19
ttcgtcaatc aacacttgtg tggtagtgac ttggcagagg ctttgtactt ggtctgtggt      60
gagagaggat tcttctacac ccctaaggct gctaagggaa tcgttgagca atgctgtact     120
tccatctgct cannnnnnca attggagaac tactgcaact aa                        162

<210> SEQ ID NO 20
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 20
ttcgtcaatc aacacttgtg tggtagtgac ttggcagagg cattgtactt ggtctgtggt      60
gagagaggat tcttctacac cccaaaggag tggaagggta tcgttgagca atgttgtgaa     120
tccatctgct cannnnnnca attggagaac tactgcaact aa                        162

<210> SEQ ID NO 21
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 21
```
ttcgtcaatc aacacttgtg tggtagtgac ttggcagagg cattgtactt ggtctgtggt     60
gagagaggat agttctacac cccaaaggag tggaagggta tcgttgagca atgttgtact    120
tccatctgct cannnnnnca attggagaac tactgcaact aa                      162

<210> SEQ ID NO 22
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 22
ttcgtcaatc aacacttgtg tggtagtgac ttggcagagg cattgtactt ggtctgtggt     60
gagagaggat agttctacac cccaaaggag tggaagggta tcgttgagca atgttgtgaa    120
tccatctgct cannnnnnca attggagaac tactgcaact aa                      162

<210> SEQ ID NO 23
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 23
aargtcaatc aacacttgtg tggtagtgac ttggcagagg cattgtactt ggtctgtggt     60
gagagaggat tcttctacac cccaaaggag tggaagggta tcgttgagca atgttgtact    120
tccatctgct cannnnnnca attggagaac tactgcaact aa                      162

<210> SEQ ID NO 24
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 24
aargtcaatc aacacttgtg tggtagtgac ttggcagagg ctttgtactt ggtctgtggt     60
gagagaggat tcttctacac ccctaaggct gctaagggaa tcgttgagca atgctgtact    120
tccatctgct cannnnnnca attggagaac tactgcaact aa                      162

<210> SEQ ID NO 25
<211> LENGTH: 162

```
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 25
aargtcaatc aacacttgtg tggtagtgac ttggcagagg cattgtactt ggtctgtggt      60
gagagaggat tcttctacac cccaaaggag tggaagggta tcgttgagca atgttgtgaa     120
tccatctgct cannnnnnca attggagaac tactgcaact aa                       162

<210> SEQ ID NO 26
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 26
aargtcaatc aacacttgtg tggtagtgac ttggcagagg cattgtactt ggtctgtggt      60
gagagaggat agttctacac cccaaaggag tggaagggta tcgttgagca atgttgtact     120
tccatctgct cannnnnnca attggagaac tactgcaact aa                       162

<210> SEQ ID NO 27
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 27
aargtcaatc aacacttgtg tggtagtgac ttggcagagg cattgtactt ggtctgtggt      60
gagagaggat agttctacac cccaaaggag tggaagggta tcgttgagca atgttgtgaa     120
tccatctgct cannnnnnca attggagaac tactgcaact aa                       162

<210> SEQ ID NO 28
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
```

<223> OTHER INFORMATION: NNN is TAT, TAC, GAA or GAG

<400> SEQUENCE: 28

```
ttcaaraatc aacacttgtg tggtagtgac ttggcagagg cattgtactt ggtctgtggt      60
gagagaggat tcttctacac cccaaaggag tggaaaggta tcgttgagca atgttgtact     120
tccatctgct cannnnnnca attggagaac tactgcaact aa                        162
```

<210> SEQ ID NO 29
<211> LENGTH: 161
<212> TYPE: DNA
<213> ORGANISM: Homo sapiens
<220> FEATURE:
<221> NAME/KEY: misc_feature
<222> LOCATION: (132)..(134)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (135)..(137)
<223> OTHER INFORMATION: NNN is TAT, TAC, GAA or GAG

<400> SEQUENCE: 29

```
ttcaaratca acacttgtgt ggtagtgact tggcagaggc tttgtacttg gtctgtggtg      60
agagaggatt cttctacacc cctaaggctg ctaagggaat cgttgagcaa tgctgtactt    120
ccatctgctc annnnnncaa ttggagaact actgcaacta a                         161
```

<210> SEQ ID NO 30
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 30

```
ttcaaraatc aacacttgtg tggtagtgac ttggcagagg cattgtactt ggtctgtggt      60
gagagaggat tcttctacac cccaaaggag tggaaaggta tcgttgagca atgttgtgaa    120
tccatctgct cannnnnnca attggagaac tactgcaact aa                        162
```

<210> SEQ ID NO 31
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 31

```
ttcaaraatc aacacttgtg tggtagtgac ttggcagagg cattgtactt ggtctgtggt      60
gagagaggat agttctacac cccaaaggag tggaaaggta tcgttgagca atgttgtact    120
tccatctgct cannnnnnca attggagaac tactgcaact aa                        162
```

<210> SEQ ID NO 32
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 32
ttcaaraatc aacacttgtg tggtagtgac ttggcagagg cattgtactt ggtctgtggt      60
gagagaggat agttctacac cccaaaggag tggaagggta tcgttgagca atgttgtgaa     120
tccatctgct cannnnnnca attggagaac tactgcaact aa                        162

<210> SEQ ID NO 33
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 33
ttcgtcaarc aacacttgtg tggtagtgac ttggcagagg cattgtactt ggtctgtggt      60
gagagaggat tcttctacac cccaaaggag tggaagggta tcgttgagca atgttgtact     120
tccatctgct cannnnnnca attggagaac tactgcaact aa                        162

<210> SEQ ID NO 34
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 34
ttcgtcaarc aacacttgtg tggtagtgac ttggcagagg ctttgtactt ggtctgtggt      60
gagagaggat tcttctacac ccctaaggct gctaagggaa tcgttgagca atgctgtact     120
tccatctgct cannnnnnca attggagaac tactgcaact aa                        162

<210> SEQ ID NO 35
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG -continued

```
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 35
ttcgtcaarc aacacttgtg tggtagtgac ttggcagagg cattgtactt ggtctgtggt    60
gagagaggat tcttctacac cccaaaggag tggaaggta tcgttgagca atgttgtgaa    120
tccatctgct cannnnnnca attggagaac tactgcaact aa                      162

<210> SEQ ID NO 36
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 36
ttcgtcaarc aacacttgtg tggtagtgac ttggcagagg cattgtactt ggtctgtggt    60
gagagaggat agttctacac cccaaaggag tggaaggta tcgttgagca atgttgtact    120
tccatctgct cannnnnnca attggagaac tactgcaact aa                      162

<210> SEQ ID NO 37
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 37
ttcgtcaarc aacacttgtg tggtagtgac ttggcagagg cattgtactt ggtctgtggt    60
gagagaggat agttctacac cccaaaggag tggaaggta tcgttgagca atgttgtgaa    120
tccatctgct cannnnnnca attggagaac tactgcaact aa                      162

<210> SEQ ID NO 38
<211> LENGTH: 162
<212> TYPE: DNA
<213> ORGANISM: Homo sapiens

<400> SEQUENCE: 38
ttcgtcaatc aacacttgtg tggtagtgac ttggcagagg cattgtactt ggtctgtggt    60
gagagaggat tcttctacac cccagargag tggaaggta tcgttgagca atgttgtact    120
tccatctgct cattgtacca attggagaac tactgcaact aa                      162

<210> SEQ ID NO 39
<211> LENGTH: 162
<212> TYPE: DNA
<213> ORGANISM: Homo sapiens
```

<400> SEQUENCE: 39
ttcgtcaatc aacacttgtg tggtagtgac ttggcagagg ctttgtactt ggtctgtggt      60
gagagaggat tcttctacac ccctgargct gctaagggaa tcgttgagca atgctgtact     120
tccatctgct cattgtacca attggagaac tactgcaact aa                        162

<210> SEQ ID NO 40
<211> LENGTH: 162
<212> TYPE: DNA
<213> ORGANISM: Homo sapiens

<400> SEQUENCE: 40
ttcgtcaatc aacacttgtg tggtagtgac ttggcagagg cattgtactt ggtctgtggt      60
gagagaggat tcttctacac cccagargag tggaagggta tcgttgagca atgttgtgaa     120
tccatctgct cattgtacca attggagaac tactgcaact aa                        162

<210> SEQ ID NO 41
<211> LENGTH: 162
<212> TYPE: DNA
<213> ORGANISM: Homo sapiens

<400> SEQUENCE: 41
ttcgtcaatc aacacttgtg tggtagtgac ttggcagagg cattgtactt ggtctgtggt      60
gagagaggat agttctacac cccagargag tggaagggta tcgttgagca atgttgtact     120
tccatctgct cattgtacca attggagaac tactgcaact aa                        162

<210> SEQ ID NO 42
<211> LENGTH: 162
<212> TYPE: DNA
<213> ORGANISM: Homo sapiens

<400> SEQUENCE: 42
ttcgtcaatc aacacttgtg tggtagtgac ttggcagagg cattgtactt ggtctgtggt      60
gagagaggat agttctacac cccagargag tggaagggta tcgttgagca atgttgtgaa     120
tccatctgct cattgtacca attggagaac tactgcaact aa                        162

<210> SEQ ID NO 43
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 43
ttcgtcaatc aacacttgtg tggtagtgac ttggcagagg cattgtactt ggtctgtggt      60
gagagaggat tcttctacac cccagargag tggaagggta tcgttgagca atgttgtact     120
tccatctgct cannnnnnca attggagaac tactgcaact aa                        162

<210> SEQ ID NO 44
<211> LENGTH: 162
<212> TYPE: DNA
<213> ORGANISM: Homo sapiens
<220> FEATURE:

```
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 44
ttcgtcaatc aacacttgtg tggtagtgac ttggcagagg ctttgtactt ggtctgtggt       60
gagagaggat tcttctacac ccctgargct gctaagggaa tcgttgagca atgctgtact      120
tccatctgct cannnnnnca attggagaac tactgcaact aa                         162

<210> SEQ ID NO 45
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 45
ttcgtcaatc aacacttgtg tggtagtgac ttggcagagg cattgtactt ggtctgtggt       60
gagagaggat tcttctacac cccagargag tggaagggta tcgttgagca atgttgtgaa      120
tccatctgct cannnnnnca attggagaac tactgcaact aa                         162

<210> SEQ ID NO 46
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 46
ttcgtcaatc aacacttgtg tggtagtgac ttggcagagg cattgtactt ggtctgtggt       60
gagagaggat agttctacac cccagargag tggaagggta tcgttgagca atgttgtact      120
tccatctgct cannnnnnca attggagaac tactgcaact aa                         162

<210> SEQ ID NO 47
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 47
```
ttcgtcaatc aacacttgtg tggtagtgac ttggcagagg cattgtactt ggtctgtggt        60
gagagaggat agttctacac cccagargag tggaagggta tcgttgagca atgttgtgaa      120
tccatctgct cannnnnnca attggagaac tactgcaact aa                        162

<210> SEQ ID NO 48
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 48
gargtcaatc aacacttgtg tggtagtgac ttggcagagg cattgtactt ggtctgtggt        60
gagagaggat tcttctacac cccaagarag tggaagggta tcgttgagca atgttgtact      120
tccatctgct cannnnnnca attggagaac tactgcaact aa                        162

<210> SEQ ID NO 49
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 49
gargtcaatc aacacttgtg tggtagtgac ttggcagagg ctttgtactt ggtctgtggt        60
gagagaggat tcttctacac ccctagarct gctaagggaa tcgttgagca atgctgtact      120
tccatctgct cannnnnnca attggagaac tactgcaact aa                        162

<210> SEQ ID NO 50
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 50
gargtcaatc aacacttgtg tggtagtgac ttggcagagg cattgtactt ggtctgtggt        60
gagagaggat tcttctacac cccaagarag tggaagggta tcgttgagca atgttgtgaa      120
tccatctgct cannnnnnca attggagaac tactgcaact aa                        162

<210> SEQ ID NO 51
<211> LENGTH: 161

```
<212> TYPE: DNA
<213> ORGANISM: Homo sapiens
<220> FEATURE:
<221> NAME/KEY: misc_feature
<222> LOCATION: (132)..(134)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (135)..(137)
<223> OTHER INFORMATION: NNN is TAT, TAC, GAA or GAG

<400> SEQUENCE: 51
gargtcaatc aacacttgtg tggtagtgac ttggcagagg cattgtactt ggtctgtggt      60
gagagaggat agttctaccc ccaagaragt ggaagggtat cgttgagcaa tgttgtactt     120
ccatctgctc annnnnncaa ttggagaact actgcaacta a                         161

<210> SEQ ID NO 52
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 52
gargtcaatc aacacttgtg tggtagtgac ttggcagagg cattgtactt ggtctgtggt      60
gagagaggat tagttctacc cccaagarag tggaagggta tcgttgagca atgttgtgaa    120
tccatctgct cannnnnnca attggagaac tactgcaact aa                        162

<210> SEQ ID NO 53
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 53
ttcgaraatc aacacttgtg tggtagtgac ttggcagagg cattgtactt ggtctgtggt      60
gagagaggat tcttctacac cccaagarag tggaagggta tcgttgagca atgttgtact    120
tccatctgct cannnnnnca attggagaac tactgcaact aa                        162

<210> SEQ ID NO 54
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
```

<223> OTHER INFORMATION: NNN is TAT, TAC, GAA or GAG

<400> SEQUENCE: 54
ttcgaraatc aacacttgtg tggtagtgac ttggcagagg ctttgtactt ggtctgtggt     60
gagagaggat tcttctacac ccctagarct gctaagggaa tcgttgagca atgctgtact   120
tccatctgct cannnnnnca attggagaac tactgcaact aa                     162

<210> SEQ ID NO 55
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 55
ttcgaraatc aacacttgtg tggtagtgac ttggcagagg cattgtactt ggtctgtggt     60
gagagaggat tcttctacac cccaagarag tggaagggta tcgttgagca atgttgtgaa   120
tccatctgct cannnnnnca attggagaac tactgcaact aa                     162

<210> SEQ ID NO 56
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 56
ttcgaraatc aacacttgtg tggtagtgac ttggcagagg cattgtactt ggtctgtggt     60
gagagaggat agttctacac cccaagarag tggaagggta tcgttgagca atgtttgtact   120 tccatctgct cannnnnnca attggagaac tactgcaact aa                     162

<210> SEQ ID NO 57
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 57
ttcgaraatc aacacttgtg tggtagtgac ttggcagagg cattgtactt ggtctgtggt     60
gagagaggat agttctacac cccaagarag tggaagggta tcgttgagca atgttgtgaa   120
tccatctgct cannnnnnca attggagaac tactgcaact aa                     162

<210> SEQ ID NO 58
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 58
ttcgtcgarc aacacttgtg tggtagtgac ttggcagagg cattgtactt ggtctgtggt      60
gagagaggat tcttctacac cccagargag tggaaggta tcgttgagca atgttgtact      120
tccatctgct cannnnnnca attggagaac tactgcaact aa                         162

<210> SEQ ID NO 59
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 59
ttcgtcgarc aacacttgtg tggtagtgac ttggcagagg ctttgtactt ggtctgtggt      60
gagagaggat tcttctacac ccctgargct gctaagggaa tcgttgagca atgctgtact      120
tccatctgct cannnnnnca attggagaac tactgcaact aa                         162

<210> SEQ ID NO 60
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 60
ttcgtcgarc aacacttgtg tggtagtgac ttggcagagg cattgtactt ggtctgtggt      60
gagagaggat tcttctacac cccagargag tggaaggta tcgttgagca atgttgtgaa      120
tccatctgct cannnnnnca attggagaac tactgcaact aa                         162

<210> SEQ ID NO 61
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or TGG

```
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 61
ttcgtcgarc aacacttgtg tggtagtgac ttggcagagg cattgtactt ggtctgtggt      60
gagagaggat agttctacac cccagargag tggaagggta tcgttgagca atgttgtact     120
tccatctgct cannnnnnca attggagaac tactgcaact aa                       162

<210> SEQ ID NO 62
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC, or
      TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 62
ttcgtcgarc aacacttgtg tggtagtgac ttggcagagg cattgtactt ggtctgtggt      60
gagagaggat agttctacac cccagargag tggaagggta tcgttgagca atgttgtgaa    120
tccatctgct cannnnnnca attggagaac tactgcaact aa                       162
```

US 10,822,386 B2

INSULIN ANALOGUES WITH ENHANCED STABILITY AND REDUCED MITOGENICITY

STATEMENT REGARDING FEDERALLY SPONSORED RESEARCH OR DEVELOPMENT

This invention was made with government support under Grant Nos. DK074176, DK040949, and DK0792333 awarded by the National Institutes of Health. The U.S. government has certain rights in the invention.

BACKGROUND OF THE INVENTION

This invention relates to polypeptide hormone analogues that exhibit enhanced pharmaceutical properties, such as increased thermodynamic stability, decreased mitogenicity, and feasibility of a rapid-acting formulation at high protein concentrations (1-5 mM) in the absence of zinc ions. More particularly, this invention relates to insulin analogues that confer rapid action at increased formulation strengths (relative to wild-type insulin) and/or that exhibit increased biological potency per nanomole of the hormone analogue administered to a patient (relative to wild-type insulin). The analogues of the present invention thus consist of two polypeptide chains that contain a novel combination of amino-acid substitutions such that the analogues exhibit (i) enhanced thermodynamic stability, (ii) decreased self-association at protein concentrations greater than 0.6 mM, and (iii) biological potency equal to or greater than that of wild-type human insulin on a nanomolar basis, i.e., that, relative to wild-type human insulin, fewer molecules of the insulin analogue are required, on subcutaneous or intravenous injection in a mammal, to elicit a similar reduction in blood-glucose concentration.

The engineering of non-standard proteins, including therapeutic agents and vaccines, may have broad medical and societal benefits. Naturally occurring proteins—as encoded in the genomes of human beings, other mammals, vertebrate organisms, invertebrate organisms, or eukaryotic cells in general—may have evolved to function optimally within a cellular context but may be suboptimal for therapeutic applications. Analogues of such proteins may exhibit improved biophysical, biochemical, or biological properties. A benefit of protein analogues would be to achieve enhanced "on-target" activity (such as metabolic regulation of metabolism leading to reduction in blood-glucose concentration) with decreased unintended and unfavorable side effects, such as promotion of the growth of cancer cells. Another benefit of such protein engineering would be preservation of rapid onset of action on concentration of the protein to achieve formulations of higher strength. Yet another example of a societal benefit would be augmented resistance to degradation at or above room temperature, facilitating transport, distribution, and use. An example of a therapeutic protein is provided by insulin. Wild-type human insulin and insulin molecules encoded in the genomes of other mammals bind to insulin receptors is multiple organs and diverse types of cells, irrespective of the receptor isoform generated by alternative modes of RNA splicing or by alternative patterns of post-translational glycosylation. Wild-type insulin also binds with lower but significant affinity to the homologous Type 1 insulin-like growth factor receptor (IGF-1R).

Insulin is a two-chain protein molecule that in a vertebrate animal is the biosynthetic product of a single-chain precursor, designated proinsulin. The sequence and structure of human proinsulin (SEQ ID NO: 1) are illustrated in FIGS. 1A and 1B, respectively; the sequence of human insulin is shown in FIG. 1C. The two polypeptide chains of insulin are respectively designated A and B, SEQ ID NOS: 2 and 3 respectively. Specific residues in one or the other chain are designated below by standard three letter code (for example, Ala for Alanine or Asp for Aspartic Acid) followed by a superscript that designates the chain (A or B) and residue number in that chain. For example, Histidine at position 10 of the B chain is designated $His^{B10}$, Valine at position 12 of the B chain is designated $Val^{B12}$, and Threonine at position 8 of the A chain is designated $Thr^{A8}$. "Insulin analogues" designate a class of molecules related to wild-type insulin by substitution of one more amino-acid residues by a different type of amino acid or by modifications of one or more atoms in the side chain or main chain of such residues by a different atom or set of atoms. An example of an insulin analogue known in the art is insulin lispro, in which $Pro^{B28}$ is substituted by Lys and $Lys^{B29}$ is substituted by Pro. Insulin lispro (also designated KP-insulin) is the active component of the product Humalog® (Eli Lilly and Co.).

It is known in the art that the B chain of insulin may be modified through standard amino-acid substitutions at one or a few positions to enhance the rate of absorption of an insulin analogue formulation from the subcutaneous depot. An example of a further medical benefit would be optimization of the pharmacokinetic properties of a soluble insulin analogue formulation such that rapid onset of action is retained in formulations of strengths in the range U-200 through U-1000, i.e., between twofold and tenfold higher than conventional U-100 insulin products (in this nomenclature "U-X" designates X internal units per ml of solution or suspension). Insulin formulations of increased strength promise to be of particular benefit for patients who exhibit marked insulin resistance and may also be of value in internal or external insulin pumps, either to extend the reservoir life or to permit miniaturization of the reservoir in a new generation of pump technologies. Existing insulin products typically exhibit prolonged pharmacokinetic and pharmacodynamics properties on increasing the concentration of the insulin or insulin analogue to achieve formulation strengths >U-200 (200 international units/ml). Such prolongation impairs the efficacy of such products for the prandial control of glycemia on subcutaneous injection and impairs the efficacy and safety of pump-based continuous subcutaneous infusion. In light of these disadvantages, the therapeutic and societal benefits of rapid-acting insulin analogue formulations would be enhanced by the engineering of insulin analogues that retain rapid action at strengths between U-200 and U-1000. Additional benefits would accrue if the novel soluble insulin analogue exhibited weaker affinity for the Type 1 IGF receptor relative to wild-type human insulin. Still additional therapeutic and societal benefit would accrue if the concentrated insulin analogue formulation should exhibit reduced mitogenicity in assays developed to monitor insulin-stimulated proliferation of human cancer cell lines.

Administration of insulin has long been established as a treatment for diabetes mellitus. A major goal of conventional insulin replacement therapy in patients with diabetes mellitus is tight control of the blood glucose concentration to prevent its excursion above or below the normal range characteristic of healthy human subjects. Excursions below the normal range are associated with immediate adrenergic or neuroglycopenic symptoms, which in severe episodes lead to convulsions, coma, and death. Excursions above the normal range are associated with increased long-term risk of microvascular disease, including retinapathy, blindness, and renal failure.

Insulin is a small globular protein that plays a central role in metabolism in vertebrates. Insulin contains two chains, an A chain, containing 21 residues, and a B chain containing 30 residues. The hormone is stored in the pancreatic β-cell as a $Zn^{2+}$-stabilized hexamer, but functions as a $Zn^{2+}$-free monomer in the bloodstream. Insulin is the product of a single-chain precursor, proinsulin, in which a connecting region (35 residues) links the C-terminal residue of B chain (residue B30) to the N-terminal residue of the A chain. A variety of evidence indicates that it consists of an insulin-like core and disordered connecting peptide. Formation of three specific disulfide bridges (A6-A11, A7-B7, and A20-B19) is coupled to oxidative folding of proinsulin in the rough endoplasmic reticulum (ER). Proinsulin is converted to insulin in the trans-Golgi network en route to storage as zinc insulin hexamers in the glucose-regulated secretory granules within pancreatic beta-cells.

The present invention was motivated by medical and societal needs to engineer a rapid-acting insulin analogue in a soluble formulation at neutral pH at strengths in the range U-200 through U-1000. A barrier to such products has long been posed by the complex self-association properties of wild-type insulin, which at neutral pH can form a concentration-dependent distribution of monomeric, dimeric, trimeric, tetrameric, hexameric, dodecameric, and higher-order species. Traditional insulin formulations known in the art typically employ a predominance of zinc insulin hexamers at a nominal protein concentration, in monomer units, of 0.6 mM (lower on dilution), whose stable assembly protects the hormone from physical and chemical degradation. Concentrating wild-type insulin hexamers above this protein concentration leads to progressive hexamer-hexamer interactions; this further level of self-association is associated with delayed absorption of the injected insulin from a subcutaneous depot, leading in turn to prolonged pharmacokinetics and pharmacodynamics. Analogous prolongation of current prandial insulin analogue products (Humalog®, Novolog® and Apidra®) occurs on their concentration above ca. 2 mM (in monomer units). To overcome this barrier, we envisaged a novel route toward the engineering of a rapid-acting insulin analogue formulation with increased strength. The first approach was to design ultra-stable insulin monomers and dimers refractory to significant higher-order self-assembly even at protein concentrations as high as 3-8 mM. In this approach the augmented intrinsic stability of the individual insulin analogue molecule would render its zinc-mediated or zinc-independent hexamer assembly unnecessary for a stable formulation, i.e., in accordance with guidelines of the U.S. Food & Drug Administration with respect to chemical degradation, polymerization and fibrillation. The efficacy of this approach would be further enhanced by insulin analogues whose intrinsic biological activity, on a per molecule basis, would be greater than that of wild-type insulin. Enhanced intrinsic activity would enable protein solutions even at the conventional concentration of 0.6 mM (as in Humalog®, Novolog® and Apidra®) to exhibit a strength greater than U-100. Because key mechanisms of insulin degradation are more rapid in concentrated protein solutions than in dilute protein solutions, higher intrinsic potency would also enhance formulation stability relative to a corresponding insulin analogue formulation of the same strength but higher protein concentration. Although thus of incremental benefit to the present invention, enhanced potency in itself is not an essential feature of the present invention.

An insulin analogue known in the art to exhibit enhanced intrinsic stability in the absence of zinc ions and decreased self-assembly beyond the dimer is provided by $Asp^{B10}$-insulin. The wild-type residue ($His^{B10}$) functions in native hexamer assembly to coordinate the two axial zinc ions in the central axis of the hexamer. Substitution of $His^{B10}$ by Asp impairs the binding of zinc ions in this axial mode and blocks higher-order self-assembly via the trimer-related surface of the classical hexamer. $Asp^{B10}$ may be expected on general grounds by enhance the segmental stability of the central B-chain α-helix in the zinc-free monomer or dimer via electrostatic mechanisms: as a favorable C-Cap residue. Irrespective of the theoretical underpinnings of protein stability, substitution of $His^{B10}$ by Asp was observed indeed to augment the thermodynamic stability of the zinc-free insulin monomer as probed by chemical-denaturation studies. $Asp^{B10}$ also enhances the affinity of insulin for the insulin receptor and augments in parallel its potency to stimulate lipogenesis in isolated adipocytes.

Despite the above favorable properties conferred by substitution of $His^{B10}$ by Asp in wild-type insulin, its clinical use was precluded by increased mitogenicity in cell-culture assays of neoplastic cell lines (including a cell line derived from a human breast cancer) in association with the finding of an excess incidence of mammary tumors on chronic treatment of Sprague-Dawley rats by $Asp^{B10}$-insulin relative to wild-type insulin. There is a need therefore, for an insulin analogue that provides a combination of amino-acid substitutions in the insulin molecule such that the favorable properties conferred by $Asp^{B10}$ (such as enhanced stability and impaired self-assembly beyond the stage of dimerization) are retained whereas the unfavorable increase in mitogenicity in cell-culture assay is mitigated or even reduced to achieve a level of mitogenicity equal to or lower than that of wild-type insulin itself.

SUMMARY OF THE INVENTION

It is an aspect of the present invention to provide an insulin analogue that comprises a combination of amino-acid substitutions in the insulin molecule such that the favorable properties conferred by $Asp^{B10}$ (such as enhanced stability and impaired self-assembly beyond the stage of dimerization) are retained whereas the unfavorable increase in mitogenicity in cell-culture assay is mitigated or even reduced to achieve a level of mitogenicity equal to or lower than that of wild-type insulin itself. FIG. 2 is a schematic representation of the pharmacokinetic principle underlying the design of prandial (rapid-acting) insulin analogs of the claimed invention. Whereas in a subcutaneous depot the insulin hexamer (upper left) is too large to efficiently penetrate into capillaries (bottom), more rapid uptake is mediated by the insulin dimer (center top) and insulin monomer (upper right). Prandial insulin products Humalog® and Novolog® contain insulin analogues (insulin lispro and aspart, respectively) with amino-acid substitutions at or near the dimerization surface of the zinc insulin hexamer such that its rate of disassembly is accelerated; prandial insulin product Apidra® (insulin deglulisine) is formulated as zinc-free oligomers (as a coupled equlibria) that likewise exhibit rapid rates of disassembly in the depot. The insulin analogues of the present invention provide isolated insulin monomers and weakly associating dimers whose augmented stability enables formulation in the absence of zinc-mediated assembly or zinc-free higher-order assembly. The hexamer at upper left depicts a $T_3R'_3$ zinc hexamer in which the A chain is shown in light gray, and B chain in medium gray; three bound phenolic ligands are shown as CPK models in dark gray. The dimer at center depicts a zinc-free T2 dimer in which the A chain is shown in dark gray, and B chain in light gray (residues B1-B23 and B29-B30) or medium gray (B24-B28; anti-parallel beta-sheet); dimer-related interchain hydrogen bonds are shown in dotted line. A collection of crystallographic protomers (T, R and $R^f$) is shown at upper right wherein the A chain is shown in dark gray, and B chain in medium gray (B1-B9) and light gray (B10-B30).

A surprising aspect of the present invention is that these complementary goals can be achieved by co-introduction of the acidic Asp$^{B10}$ substitution with (i) an amino-acid substitution in the central α-helix of the B chain (Val$^{B12}$→Ala) long regarded as unfavorable due to a marked decreased in the variant hormone's affinity for the insulin receptor and (ii) an amino-acid substitution in the C-terminal segment of the B chain (Lys$^{B29}$→Glu) previously paired with a basic substitution in the N-terminal segment of the B chain (Asn$^{B3}$→Lys) for an unrelated purpose, to whit, design of a prandial insulin analog competent for self-assembly. The insulin analogues of the present invention thus contain as a core design element the three substitutions Asp$^{B10}$, Ala$^{B12}$ and Glu$^{B29}$ based on our surprising observation that this combination retains the advantageous properties of Asp$^{B10}$ while mitigating or avoiding its disadvantageous properties. Insulin analogues of the present invention may also contain non-β-branched substitutions at position A8, halogenated derivatives of Phenylalanine at position B24, or C-terminal extensions of the B chain to include residue B31 (a 31-residue B-chain or residues B31-B32 (a 32-residue B chain). The above set of analogues may optionally further be modified by deletion of N-terminal B-chain residues B1, B1-B2, or B1-B3.

It is a second surprising aspect of the present invention is that insulin analogues can at the same time be designed to exhibit impaired self-assembly—and therefore rapid action on subcutaneous assembly—and yet maintain sufficient stability with respect to chemical and physical degradation as to permit their safe and effective formulation as a practical insulin product. It comes as a further surprise that the above may be accompanied by no elevation in their mitogenicity. We envisage that the products of the present invention will disproportionately benefits patients in Western societies with obesity, Type 2 diabetes mellitus and marked insulin resistance. Such clinical features pose a growing burden to under-represented minorities, including African-Americans, Hispanic-Americans and indigenous American tribes. Due to their enhanced biological activity per nanomole of protein, products of the present invention will also be useful in extending the reservoir life of insulin pumps and in enabling the miniaturization of such pumps.

It is, furthermore, an aspect of the present invention to provide insulin analogues that provide rapid-acting pharmacokinetic and pharmacodynamics properties on subcutaneous injection. The analogues of the present invention contain Aspartic Acid at position B10 (Asp$^{B10}$), Alanine at position B12 (Ala$^{B12}$), and Glutamic Acid at B29 (Glu$^{B29}$); optionally, such analogues may contain a non-β-branched amino-acid substitution at position A8, a halogenic derivative of the aromatic ring of Phenylalanine at B24, a C-terminal extension of the B chain up to and including two residues (B31 and B32), and/or an N-terminal deletion of the B chain up to and including three residues (B1-B3). Residue B28 may be Pro (as in wild-type insulin), Lys, Gln, or Ala. Position A13 may optionally be Leu, Trp or Tyr; position A14 may optionally be Tyr or Glu. Residue B30 may optionally be absent. The insulin analogs of the present invention may also contain one or more halogen atoms (fluorine, chlorine, bromine, or iodine; F, Cl, Br or I, respectively) in the aromatic ring of Phenylalanine at position B24 (such as at the ortho (or 2) position of the aromatic ring), may optionally contain standard or non-standard amino-acid substitutions at other sites in the A or B domains, such as positions B28 known in the art to confer rapid action, and may optionally contain one- or two-residue extensions of the B chain (residues B31 and B32). It is an additional aspect of the present invention that the analogues exhibit thermodynamic stabilities equal to or greater than that of wild-type human insulin, and mitogenicities in a tissue-culture assay of a human breast-cancer cell line equal to or less than that of wild-type human insulin.

The above combination of features is conferred by a novel combination of acidic amino-acid substitutions at positions B10 and B29 in concert with Alanine at position B12. Although not wishing to be constrained by theory, we believe that the substitution of Val$^{B12}$ by Alanine at B12 creates at destabilizing cavity at the hormone-receptor interface, mitigating the effect of Asp$^{B10}$ to prolong the residence time and enhance the affinity of the three homologous hormone-receptor complexes (IR-A, IR-B and IGF-1R). We further believe that in the free hormone, the substitution of Val$^{B12}$ by Alanine at B12 preserves the stabilizing effects of Asp$^{B10}$ as known in the art. Although not wishing to be constrained by theory, we envision that any structural perturbation to the native Val$^{B12}$-Tyr$^{B26}$ interaction caused by the Ala$^{B12}$ substitution is balanced by the stabilizing effect of replacing a β-branched residue in an α-helix (Val$^{B12}$) by a helix-stabilizing residue (Ala$^{B12}$). Also without wishing to be constrained by theory, we further believe that non-additive effects of Ala$^{B12}$ and Glu$^{B29}$ attenuates mitogenic signaling by the complex of such analogues and the insulin receptor or by complexes of such analogues with the Type 1 IGF receptor.

In general, the present invention provides an insulin analogue containing Aspartic Acid at position B10, Alanine at position B12, Glutamic Acid at position B29, optionally other amino-acid substitutions at one or more of the following three positions: A8, A14, and B28, and optionally C-terminal extension of the B chain (to include B31 or B31-B32 where at least one of the additional residues is acidic), or N-terminal deletion of the B chain (up to and including B3). The present invention thus pertains to a novel class of insulin analogues containing a combination of modifications that together provide the long-sought clinical advantages not conferred by any one of the constituent modifications. In another version of the present invention residue B30 is absent. In yet another version the analogs of the present invention may contain Glutamic Acid at position A14, and/or Glycine, Alanine or Aspartic Acid at position A21.

BRIEF DESCRIPTION OF THE SEVERAL VIEWS OF THE DRAWINGS

FIG. 1B is a structural model of proinsulin, consisting of an insulin-like moiety and a disordered connecting peptide (dashed line).

FIG. 3A Symbols—(♦) diluent control, (■) Humalog (insulin lispro), (▲) $Asp^{B10}$, $Ala^{B12}$, $Glu^{B29}$-insulin (T-0334), and (●) $Asp^{B10}$ derivative of insulin lispro ("DKP-insulin"). FIG. 3B Symbols—(♦) diluent control, (■) Humalog (insulin lispro), (✸) $Glu^{A8}$, $Asp^{B10}$, $Ala^{B12}$, $Glu^{B29}$-insulin (T-0181), (○) $Glu^{B31}$, $Glu^{B32}$-extended version of $Glu^{A8}$, $Asp^{B10}$, $Ala^{B12}$, $Glu^{B29}$-insulin (T-0182), and (●) 2F-$Phe^{B24}$ derivative of $Glu^{A8}$, $Asp^{B10}$, $Ala^{B12}$, $Glu^{B29}$-insulin (T-0184). Error bars show standard errors.

(FIG. 4A)—Comparison of $Glu^{A8}$, $Asp^{B10}$, $Ala^{B12}$, $Glu^{B29}$-insulin (T-0181) with human insulin (labeled "HI"), insulin lispro ("KP"), $Asp^{B10}$-insulin ("AspB10"; far right) and insulin-free medium along ("basal"; far left). (FIG. 4B) Comparison of $Asp^{B10}$, $Ala^{B12}$, $Glu^{B29}$-insulin (T-0334) with the same control set. Brackets and asterisks indicate p-values less than 0.05 as a metric of statistical significance; numbers of replicates (N) are as specified.

(FIG. 5A)—Control studies of wild-type human insulin (labeled "HI"; thick solid line), insulin lispro ("KP"; thin solid line), and $Asp^{B10}$, $Orn^{B29}$-human insulin (dotted line). (FIG. 5B)—Comparative studies of $Asp^{B10}$, $Ala^{B12}$, $Glu^{B29}$-insulin (T-0334) and the $Glu^{A8}$ derivative of $Asp^{B10}$, $Ala^{B12}$, $Glu^{B29}$-insulin (T-0181) versus insulin lispro (KP; thin solid line). (FIG. 5C)—Comparative studies of the $Glu^{B31}$, $Glu^{B32}$-extended version of $Glu^{A8}$, $Asp^{B10}$ $Ala^{B12}$, $Glu^{B29}$-insulin (T-0182) and the 2F-$Phe^{B24}$ derivative of $Glu^{A8}$, $Asp^{B10}$, $Ala^{B12}$, $Glu^{B29}$-insulin (T-0184) versus insulin lispro (KP; thin solid line). (FIG. 5D)—Comparative studies of the four insulin analogues containing the core three substitutions of the present invention: $Asp^{B10}$, $Ala^{B12}$, and $Glu^{B29}$.

DETAILED DESCRIPTION OF THE INVENTION

Figure 1A:
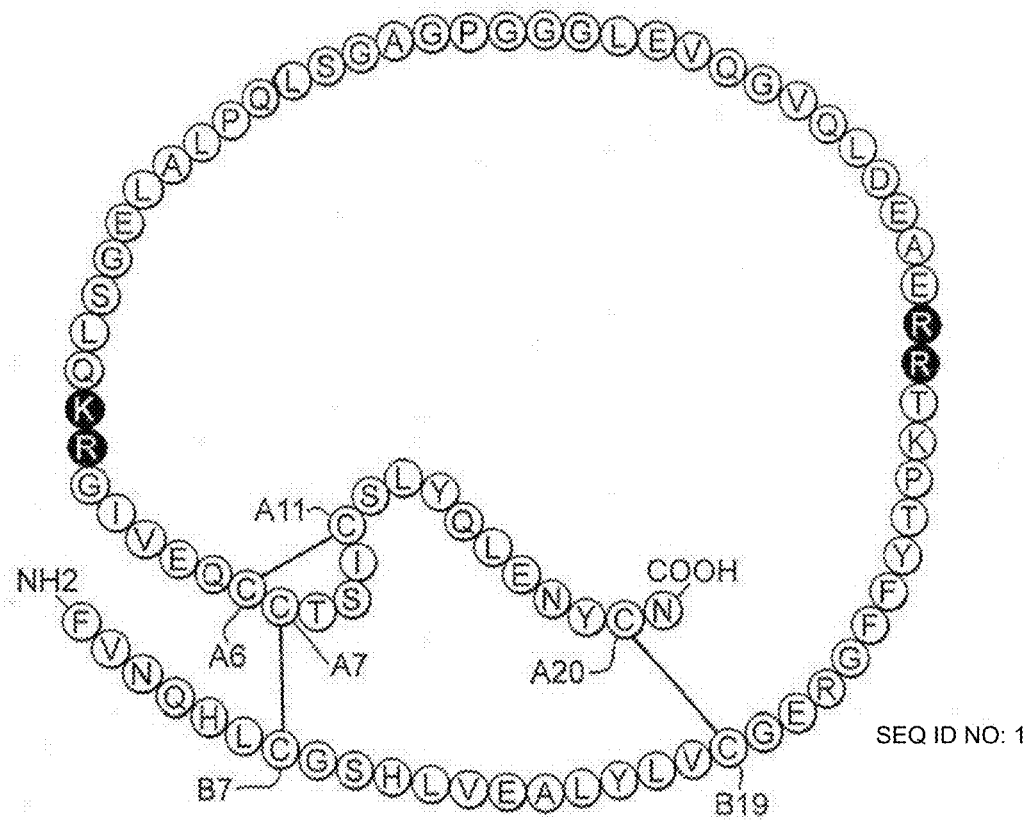
FIG. 1A is a schematic representation of the sequence of human proinsulin (SEQ ID NO: 1) including the A- and B-chains and the connecting region shown with flanking dibasic cleavage sites (filled circles) and C-peptide (open circles).
Figure 1C:
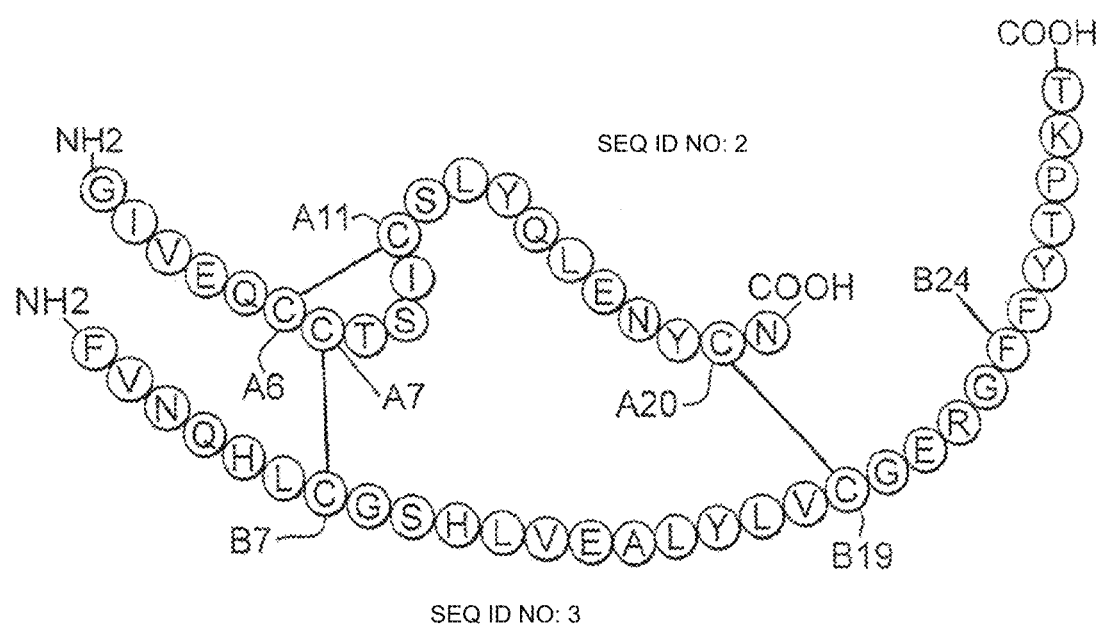
FIG. 1C is a schematic representation of the sequence of human insulin (SEQ ID NOS: 2 and 3) indicating the position of residues B27 and B30 in the B-chain.
Figure 2:
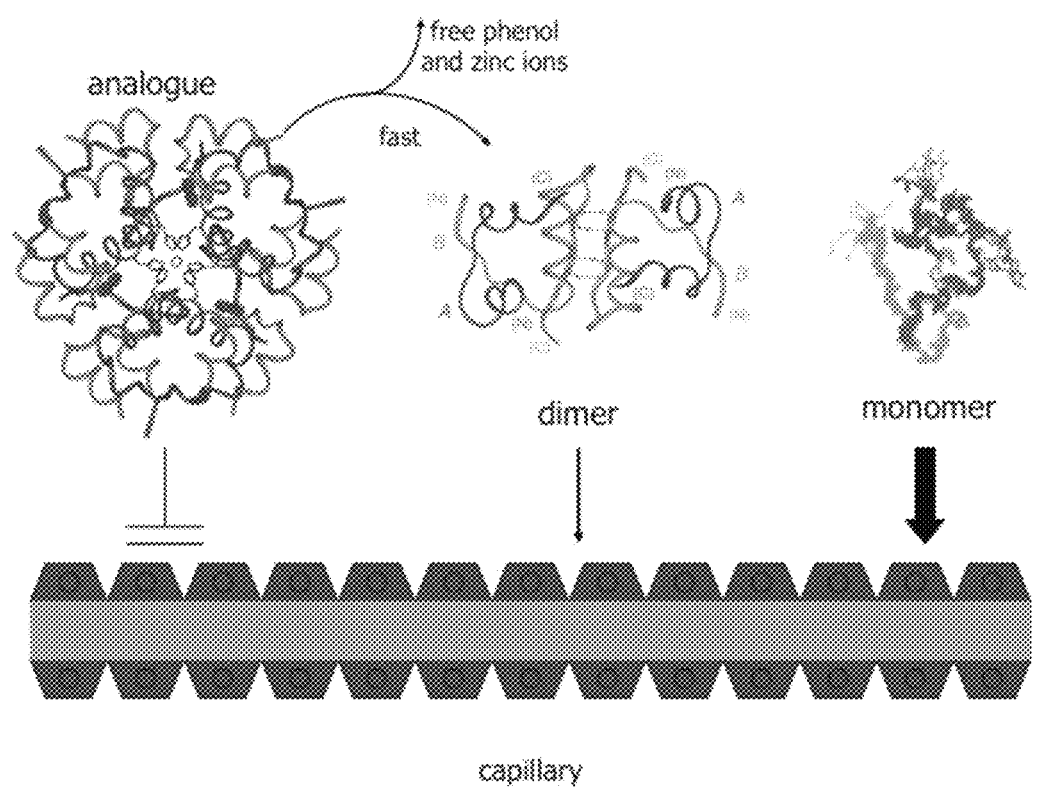
FIG. 2 is a schematic representation of the pharmacokinetic principle underlying the design of prandial (rapid-acting) insulin analogs, showing a subcutaneous depot of the insulin hexamer (upper left), capillaries (bottom), the insulin dimer (center top) and insulin monomer (upper right).

The present invention is directed toward an insulin analogue that provides enhanced in vivo biological potency on a per-molecular basis, rapid action under a broad range of protein concentrations and formulation strengths (typically from U-100 to U-500 and optionally as high as U-1000), IR-A/IR-B receptor-binding affinities with absolute affinities in the range 5-100% relative to the affinities of wild-type human (the lower limit chosen to correspond to proinsulin), affinity for the IGF-1R no greater than that of wild-type human insulin, and thermodynamic stability in the absence of zinc ions that is equal to or greater than that of wild-type human insulin relative to the baseline stability of wild-type human insulin in the absence of zinc ions.

It is a feature of the present invention that rapid absorption kinetics from a subcutaneous depot may be generated by an insulin analogue that is monomeric or dimeric—but not is a higher-order state of self-assembly—in a zinc-free solution at neutral pH at a protein concentration of 0.6-6.0 mM (as calculated in relation to the formal monomer concentration). Conventional prandial products, as known in the art, represent a continuum of possible coupled equilibria between states of self-assembly, including zinc-stabilized or zinc-ion-independent hexamers extended by potential hexamer-hexamer interactions. Molecular implementation of this strategy provides a novel class of insulin analogues that (i) are as stable or more stable as a zinc-free monomer and dimer relative to wild-type human insulin and (ii) retain at least a portion of the biological potency of wild-type human insulin (as assessed by hormone-regulated reduction in blood-glucose concentration) on a per-molecular or per-nanomole basis. It is a feature of the present invention that retained potency in relation to glycemic control is associated with reduced mitogenicity, which is a biological consequence of a distinct signaling pathway that is undesirable from the perspective of cancer risk and cancer growth.

It is also envisioned that insulin analogues may be made with A- and B chain sequences derived from animal insulins, such as porcine, bovine, equine, and canine insulins, by way of non-limiting examples, so long as an Aspartic Acid is retained at position B10, Alanine is present at position B12, Glutamic Acid is present at position B29, a halogenated derivative of Phenylalanine is optionally present at position B24, and one or more acidic amino-acid substitutions are optionally present at one or more of the sites provided by A8, A14, A21, and B28. Such variant B chains derived from human insulin or animal insulins may optionally lack $Thr^{B30}$ (des-B30) or contain a C-terminal dipeptide extension (with respective residue positions designated B31 and B32) wherein at least one of these C-terminal extended residues is an acidic amino acid. In addition or in the alternative, the insulin analogue of the present invention may contain a deletion of residues B1, B1-B2, or B1-B3; or may be combined with a variant B chain lacking Proline at position B28 (e.g., $Lys^{B28}$, $Ala^{B28}$ or $Gln^{B28}$ in combination with Glutamic Acid at position B29). At position A13 may optionally be substituted by Trp or Tyr, position A14 Tyrosine may optionally be substituted by Glutamic Acid, and at position A21 Asparagine may optionally be substituted by Alanine, Glycine or Aspartic Acid.

It is further envisioned that the insulin analogues of the present invention may be derived from Lys-directed proteolysis of a precursor polypeptide in yeast biosynthesis in *Pichia pastoris, Saccharomyces cerevisciae*, or other yeast expression species or strains. Such strains may be engineered to insert halogen-modified Phenylalanine at position B24 by means of an engineered tRNA synthetase and orthogonal nonsense suppression. The halogenic modification at position B24 may be at the 2-ring position of $Phe^{B24}$ (i.e., ortho-F-$Phe^{B24}$, ortho-Cl-$Phe^{B24}$, or ortho-Br-$Phe^{B24}$.

Optionally, the analogues may contain iodo-substitutions within the aromatic ring of Tyr$^{B16}$ and/or Tyr$^{B26}$ (3-mono-iodo-Tyr or [3, 5]-di-iodo-Tyr); intended to augment thermodynamic stability and receptor-binding activity). It is also envisioned that Thr$^{B27}$, Thr$^{B30}$, or one or more Serine residues in the C-domain may be modified, singly or in combination, by a monosaccaride adduct; examples are provided by O-linked N-acetyl-β-D-galactopyranoside (designated GalNAc-O$^β$-Ser or GalNAc-O$^β$-Thr), O-linked α-D-mannopyranoside (mannose-O$^β$-Ser or mannose-O$^β$-Thr), and/or α-D-glucopyranoside (glucose-O$^β$-Ser or glucose-O$^β$-Thr).

Furthermore, in view of the similarity between human and animal insulins, and use in the past of animal insulins in human patients with diabetes mellitus, it is also envisioned that other minor modifications in the sequence of insulin may be introduced, especially those substitutions considered "conservative." For example, additional substitutions of amino acids may be made within groups of amino acids with similar side chains, without departing from the present invention. These include the neutral hydrophobic amino acids: Alanine (Ala or A), Valine (Val or V), Leucine (Leu or L), Isoleucine (Ile or I), Proline (Pro or P), Tryptophan (Trp or W), Phenylalanine (Phe or F) and Methionine (Met or M). Likewise, the neutral polar amino acids may be substituted for each other within their group of Glycine (Gly or G), Serine (Ser or S), Threonine (Thr or T), Tyrosine (Tyr or Y), Cysteine (Cys or C), Glutamine (Glu or Q), and Asparagine (Asn or N). Acidic amino acids are Aspartic acid (Asp or D) and Glutamic acid (Glu or E). Introduction of basic amino-acid substitutions (including Lysine (Lys or K), Arginine (Arg or R) and Histidine (His or H)) are not preferred in order to maintain the enhanced net negative charge of this class of analogues. Unless noted otherwise or wherever obvious from the context, the amino acids noted herein should be considered to be L-amino acids. Standard amino acids may also be substituted by non-standard amino acids belonging to the same chemical class.

The amino-acid sequence of human proinsulin is provided, for comparative purposes, as SEQ ID NO: 1.

```
(human proinsulin)
                                     SEQ ID NO: 1
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Thr-Arg-Arg-Glu-Ala-Glu-Asp- Leu-Gln-Val-Gly-Gln-Val-Glu-Leu-Gly-Gly-Gly-Pro- Gly-Ala-Gly-Ser-Leu-Gln-Pro-Leu-Ala-Leu-Glu-Gly- Ser-Leu-Gln-Lys-Arg-Gly-Ile-Val-Glu-Gln-Cys-Cys- Thr-Ser-Ile-Cys-Ser-Leu-Tyr-Gln-Leu-Glu-Asn-Tyr- Cys-Asn
```

The amino-acid sequence of the A chain of human insulin is provided as SEQ ID NO: 2.

```
(human A chain; residue positions A1-A21)
                                     SEQ ID NO: 2
Gly-Ile-Val-Glu-Gln-Cys-Cys-Thr-Ser-Ile-Cys-Ser- Leu-Tyr-Gln-Leu-Glu-Asn-Tyr-Cys-Asn
```

The amino-acid sequence of the B chain of human insulin is provided as SEQ ID NO: 3.

```
(human B chain; residue positions B1-B30)
                                     SEQ ID NO: 3
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Thr
```

The amino-acid sequence of a modified insulin of the present invention is given in general form in SEQ ID NOS: 4 and 5 wherein the six Cysteine residues are paired to provide three disulfide bridges as in wild-type human insulin.

```
A chain
                                     SEQ ID NO: 4
Gly-Ile-Val-Glu-Gln-Cys-Cys-Xaa1-Ser-Ile-Cys-Ser- Leu-Xaa2-Gln-Leu-Glu-Asn-Tyr-Cys-Xaa3

B chain
                                     SEQ ID NO: 5
Xaa4-Xaa5-Xaa6-Gln-His-Leu-Cys-Gly-Ser-Asp-Leu- Ala-Glu-Ala-Leu-Tyr-Leu-Val-Cys-Gly-Glu-Arg-Gly- Xaa7-Phe-Tyr-Thr-Xaa8-Glu-Thr-Xaa9-Xaa10
```

Where Xaa$_1$ (position A8) may be Thr (as in wild-type insulin), His, Glu or any other non-β-branched amino acid; where Xaa$_2$ may be Tyr (as in wild-type insulin) or Glu; where Xaa$_3$ may be Asn, Asp, Ala or Gly; where Xaa$_4$-Xaa$_5$-Xaa$_6$ may be Phe-Val-Asn as in wild-type human insulin or N-terminal deleted variants Val-Asn (des-B1), Asn (des-B1, B2) or omitted (des-B1-B3); where Xaa$_7$ is Phenylalanine or a derivative of Phenylalanine in which one or more hydrogen atoms in the aromatic ring are substituted by a halogen atom from the group fluorine (F), chlorine (C), or bromine (Br); where Xaa$_8$ (position B28) may be Pro (as in wild type), Lys, Ala, Gln; and where optionally Xaa$_9$-Xaa$_{10}$ provides a C-terminal monopeptide or dipeptide extension of the B chain such that at least one residue is an acidic side chain. It is further envisioned that position A13 may be substituted by Trp or Tyr.

The amino-acid sequences of insulin analogues of the present invention maybe, in part, given in SEQ ID NO: 5, 6, 8 and 9 (containing intact B chains), SEQ ID NO 10-12 (containing N-terminally truncated B chains) and SEQ ID NO: 7 (containing an intact A-chain), wherein for brevity only the specific modifications relative to wild-type human insulin are provided (i.e., specific examples of sequence features Xaa$_1$, Xaa$_2$, Xaa$_3$, Xaa$_4$, Xaa$_5$, Xaa$_6$, Xaa$_7$, Xaa$_8$, Xaa$_9$, and Xaa$_{10}$. Additionally or in the alternative, a C-terminal dipeptide extension of the B chain, such that at least one residue has an acidic side chain, may also be provided. In one embodiment, the C-terminal dipeptide extension is Glu-Glu. In one particular embodiment, the amino acid sequence is SEQ ID NO: 8.

```
(Asp^B10, Ala^B12, Glu^B29)
                                     SEQ ID NO: 6
Phe-Val-Asn-Gln-His-Leu-Cys-Gly-Ser-Asp-Leu-Ala-

Glu-Ala-Leu-Tyr-Leu-Val-Cys-Gly-Glu-Arg-Gly-Phe-

Phe-Tyr-Thr-Pro-Glu-Thr
```

-continued (Glu$^{48}$)
SEQ ID NO: 7
Gly-Ile-Val-Glu-Gln-Cys-Cys-Glu-Ser-Ile-Cys-Ser- Leu-Tyr-Gln-Leu-Glu-Asn-Tyr-Cys-Asn (Asp$^{B10}$, Ala$^{B12}$, Glu$^{B29}$, Glu$^{B31}$, Glu$^{B32}$)
SEQ ID NO: 8
Phe-Val-Asn-Gln-His-Leu-Cys-Gly-Ser-Asp-Leu-Ala- Glu-Ala-Leu-Tyr-Leu-Val-Cys-Gly-Glu-Arg-Gly-Phe- Phe-Tyr-Thr-Pro-Glu-Thr-Glu-Glu (Asp$^{B10}$, Ala$^{B12}$, 2F-Phe$^{B24}$, Glu$^{B29}$)
SEQ ID NO: 9
Phe-Val-Asn-Gln-His-Leu-Cys-Gly-Ser-Asp-Leu-Ala- Glu-Ala-Leu-Tyr-Leu-Val-Cys-Gly-Glu-Arg-Gly-Xaa -

Phe-Tyr-Thr-Pro-Glu-Thr

Xaa is ortho-fluoro-Phe

Analogues of the present invention may optionally contain N-terminal deletions of the B chain (des-B1, des-B1,B2 or des-B1-B3) as indicated in SEQ ID 9-12. These N-terminal residues are not required for receptor binding, but their presence in a biosynthetic single-chain precursor is thought to enhance the efficiency of native disulfide pairing in the endoplasmic reticulum and thus production yields.

(des-(B1-B3), Asp$^{B10}$, Ala$^{B12}$, Glu$^{B29}$)
SEQ ID NO: 10
Gln-His-Leu-Cys-Gly-Ser-Asp-Leu-Ala-Glu-Ala-Leu- Tyr-Leu-Val-Cys-Gly-Glu-Arg-Gly-Phe-Phe-Tyr-Thr- Pro-Glu-Thr (des-(B1-B3), Asp$^{B10}$, Ala$^{B12}$, Glu$^{B29}$, Glu$^{B31}$, Glu$^{B32}$)
SEQ ID NO: 11
Gln-His-Leu-Cys-Gly-Ser-Asp-Leu-Ala-Glu-Ala-Leu- Tyr-Leu-Val-Cys-Gly-Glu-Arg-Gly-Phe-Phe-Tyr-Thr- Pro-Glu-Thr-Glu-Glu (des-B1-B3, Asp$^{B10}$, Ala$^{B12}$, Glu$^{B29}$, 2F-Phe$^{B24}$)
SEQ ID NO: 12
Gln-His-Leu-Cys-Gly-Ser-Asp-Leu-Ala-Glu-Ala-Leu- Tyr-Leu-Val-Cys-Gly-Glu-Arg-Gly-Xaa-Phe-Tyr-Thr- Pro-Glu-Thr Xaa is ortho-fluoro-Phe Insulin analogues were synthesized as follows:

| Designation | SEQ ID NO: |
|---|---|
| T-0334 | SEQ ID NOS: 2 and 6 (Asp$^{B10}$, Ala$^{B12}$, Glu$^{B29}$-insulin) |
| T-0181 | SEQ ID NOS: 6 and 7 (Glu$^{48}$, Asp$^{B10}$, Ala$^{B12}$, Glu$^{B29}$-insulin) |
| T-0182 | SEQ ID NOS: 7 and 8 (Glu$^{48}$, Asp$^{B10}$, Ala$^{B12}$, Glu$^{B29}$, Glu$^{B31}$, Glu$^{B32}$-insulin) |
| T-0184 | SEQ ID NOS: 7 and 9 (Glu, Asp$^{B10}$, Ala$^{B12}$, 2F-Phe$^{B24}$, Glu$^{B29}$-insulin) |

The following DNA sequences encode single-chain insulin analogues with codons optimized for usage patterns in *Pichia pastoris*. These single-chain insulin analogues provide biosynthetic intermediates for the production of the above two-chain insulin analogues. In each case the final codon (AAT) represents a stop codon.

The sense strand of a gene encoding a 53-residue single-chain insulin analogue with substitutions Asp$^{B10}$, Ala$^{B12}$ and Glu$^{B30}$ and with C-domain Trp-Lys is given in SEQ ID NO: 13.

SEQ ID NO: 13
TTCGTCAATCAACACTTGTGTGGTAGTGACTTGGCAGAGGCATTGTAC

TTGGTCTGTGGTGAGAGAGGATTCTTCTACACCCCAAAGGAGTGGAAG

GGTATCGTTGAGCAATGTTGTACTTCCATCTGCTCATTGTACCAATTG

GAGAACTACTGCAACTAA

The sense strand of a gene encoding a 53-residue single-chain insulin analogue with substitutions Asp$^{B10}$, Ala$^{B12}$ and Ala$^{B30}$ and with C-domain Ala-Lys is given in SEQ ID NO: 14.

SEQ ID NO: 14
TTCGTCAATCAACACTTGTGTGGTAGTGACTTGGCAGAGGCTTTGTAC

TTGGTCTGTGGTGAGAGAGGATTCTTCTACACCCCTAAGGCTGCTAAG

GGAATCGTTGAGCAATGCTGTACTTCCATCTGCTCATTGTACCAATTG

GAGAACTACTGCAACTAA

The sense strand of a gene encoding a 53-residue single-chain insulin analogue with substitutions Asp$^{B10}$, Ala$^{B12}$, Glu$^{48}$ and Glu$^{B30}$ and with C-domain Trp-Lys is given in SEQ ID 15.

SEQ ID NO: 15
TTCGTCAATCAACACTTGTGTGGTAGTGACTTGGCAGAGGCATTGTAC

TTGGTCTGTGGTGAGAGAGGATTCTTCTACACCCCAAAGGAGTGGAAG

GGTATCGTTGAGCAATGTTGTGAATCCATCTGCTCATTGTACCAATTG

GAGAACTACTGCAACTAA

The sense strand of a gene encoding a 53-residue single-chain insulin analogue with substitution Asp$^{B10}$, Ala$^{B12}$, and Glu$^{B30}$ and with C-domain Trp-Lys such that a non-standard amino acid may be inserted through nonsense suppression at codon position B24 (TAG) is given in SEQ ID NO: 16.

SEQ ID NO: 16
TTCGTCAATCAACACTTGTGTGGTAGTGACTTGGCAGAGGCATTGTAC

TTGGTCTGTGGTGAGAGAGGATAGTTCTACACCCCAAAGGAGTGGAAG

GGTATCGTTGAGCAATGTTGTACTTCCATCTGCTCATTGTACCAATTG

GAGAACTACTGCAACTAA

The sense strand of a gene encoding a 53-residue single-chain insulin analogue with substitution Glu$^{48}$, Asp$^{B10}$, Ala$^{B12}$ and Glu$^{B30}$ and with C-domain Trp-Lys such that a non-standard amino acid may be inserted through nonsense suppression at codon position B24 (TAG) is given in SEQ ID NO: 17.

SEQ ID NO: 17
TTCGTCAATCAACACTTGTGTGGTAGTGACTTGGCAGAGGCATTGTAC

TTGGTCTGTGGTGAGAGAGGATAGTTCTACACCCCAAAGGAGTGGAAG

GGTATCGTTGAGCAATGTTGTGAATCCATCTGCTCATTGTACCAATTG

GAGAACTACTGCAACTAA

The group of synthetic genes provided in SEQ ID NOS: 18-28 provides a set of DNA sequences that optionally encode specific amino-acid substitutions at positions A13 and A14 in accordance with the amino-acid sequences specified above. It is known in the art that in the nuclear genes of yeasts, Leucine is encoded by DNA codons TTA, TTG, CTT, CTC, and CTG; that Tyrosine is encoded by DNA codons TAT and TAC; that Tryptophan is encoded by DNA codon TGG; and that Glutamic acid is encoded by DNA codons GAA and GAG.

SEQ ID NO: 18 provides the sense strand of a gene encoding a 53-residue single-chain insulin analogue with substitutions $Asp^{B10}$, $Ala^{B12}$ and $Glu^{B30}$, with C-domain Trp-Lys such that the codon at position A13 ($XXX_1$) optionally encodes Leucine, Tyrosine or Tryptophan and such that the codon at position A14 ($XXX_2$) optionally encodes Tyrosine or Glutamic Acid.

SEQ ID NO: 18
TTCGTCAATCAACACTTGTGTGGTAGTGACTTGGCAGAGGCATTGTAC

TTGGTCTGTGGTGAGAGAGGATTCTTCTACACCCCAAAGGAGTGGAAG

GGTATCGTTGAGCAATGTTGTACTTCCATCTGCTCA-$XXX_1$-$XXX_2$-C

AATTGGAGAACTACTGCAACTAA

SEQ ID NO: 19 provides the sense strand of a gene encoding a 53-residue single-chain insulin analogue with substitutions $Asp^{B10}$, $Ala^{B12}$ and $Ala^{B30}$ and with C-domain Ala-Lys such that the codon at position A13 ($XXX_1$) optionally encodes Leucine, Tyrosine or Trptophan and the codon at position A14 ($XXX_2$) optionally encodes Tyrosine or Glutamic Acid.

SEQ ID NO: 19
TTCGTCAATCAACACTTGTGTGGTAGTGACTTGGCAGAGGCTTTGTAC

TTGGTCTGTGGTGAGAGAGGATTCTTCTACACCCCTAAGGCTGCTAAG

GGAATCGTTGAGCAATGCTGTACTTCCATCTGCTCA-$XXX_1$-$XXX_2$-C

AATTGGAGAACTACTGCAACTAA

SEQ ID NO: 20 provides the sense strand of a gene encoding a 53-residue single-chain insulin analogue with substitutions $Asp^{B10}$, $Ala^{B12}$, $Glu^{A8}$ and $Glu^{B30}$ and with C-domain Trp-Lys such that the codon at position A13 ($XXX_1$) optionally encodes Leucine, Tyrosine or Trptophan and such that the codon at position A14 ($XXX_2$) optionally encodes Tyrosine or Glutamic Acid.

SEQ ID NO: 20
TTCGTCAATCAACACTTGTGTGGTAGTGACTTGGCAGAGGCATTGTAC

TTGGTCTGTGGTGAGAGAGGATTCTTCTACACCCCAAAGGAGTGGAAG

GGTATCGTTGAGCAATGTTGTGAATCCATCTGCTCA-$XXX_1$-$XXX_2$-C

AATTGGAGAACTACTGCAACTAA

SEQ ID NO: 21 provides the sense strand of a gene encoding a 53-residue single-chain insulin analogue with substitution $Asp^{B10}$, $Ala^{B12}$, and $Glu^{B30}$ and with C-domain Trp-Lys such that a non-standard amino acid may be inserted through nonsense suppression at codon position B24 (TAG), such that the codon at position A13 ($XXX_1$) optionally encodes Leucine, Tyrosine or Trptophan and such that the codon at position A14 ($XXX_2$) optionally encodes Tyrosine or Glutamic Acid.

SEQ ID NO: 21
TTCGTCAATCAACACTTGTGTGGTAGTGACTTGGCAGAGGCATTGTAC

TTGGTCTGTGGTGAGAGAGGATAGTTCTACACCCCAAAGGAGTGGAAG

GGTATCGTTGAGCAATGTTGTACTTCCATCTGCTCA-$XXX_1$-$XXX_2$-C

AATTGGAGAACTACTGCAACTAA

SEQ ID NO: 22 provides the sense strand of a gene encoding a 53-residue single-chain insulin analogue with substitution $Glu^{A8}$, $Ala^{B12}$, $Asp^{B10}$ and $Glu^{B30}$ and with C-domain Trp-Lys such that a non-standard amino acid may be inserted through nonsense suppression at codon position B24 (TAG), such that the codon at position A13 ($XXX_1$) optionally encodes Leucine, Tyrosine or Trptophan and such the codon at position A14 ($XXX_2$) optionally encodes Tyrosine or Glutamic Acid.

SEQ ID NO: 22
TTCGTCAATCAACACTTGTGTGGTAGTGACTTGGCAGAGGCATTGTAC

TTGGTCTGTGGTGAGAGAGGATAGTTCTACACCCCAAAGGAGTGGAAG

GGTATCGTTGAGCAATGTTGTGAATCCATCTGCTCA-$XXX_1$-$XXX_2$-C

AATTGGAGAACTACTGCAACTAA

The group of synthetic genes provided in SEQ ID NOS: 23-37 provides a set of DNA sequences that, in addition to the sequence features defined in SEQ ID NOS: 18-22, optionally encode a Lysine residue at one of the following three codon positions: B1 (SEQ ID NOS: 23-27), B2 (SEQ ID NOS: 28-32) or B3 (SEQ ID NOS: 33-37); such Lysine substitutions in a biosynthetic single-chain insulin precursor would enable production of insulin analogues of the present invention whose B chains contain N-terminal deletions des-B1, des-B 1, B2, or des-B1-B3 in accordance with the amino-acid sequences specified above. These N-terminal truncations are respectively directed by substitution of Lysine at positions B1, B2 or B3 in the biosynthetic single-chain insulin precursor. It is known in the art that in nuclear genes of yeasts, Lysine is encoded by DNA codons AAA and AAG. As indicated above, it is also known in the art that in the nuclear genes of yeasts, Leucine is encoded by DNA codons TTA, TTG, CTT, CTC, and CTG; that Tyrosine is encoded by DNA codons TAT and TAC; that Tryptophan is encoded by DNA codon TGG; and that Glutamic acid is encoded by DNA codons GAA and GAG.

SEQ ID NO: 23 provides the sense strand of a gene encoding a 53-residue single-chain insulin analogue with substitutions $Asp^{B10}$, $Ala^{B12}$ and $Glu^{B30}$, with C-domain Trp-Lys such that the codon at position A13 ($XXX_1$) optionally encodes Leucine, Tyrosine or Trptophan, such that the codon at position A14 ($XXX_2$) optionally encodes Tyrosine or Glutamic Acid, and such that the first codon encodes Lysine.

SEQ ID NO: 23
AARGTCAATCAACACTTGTGTGGTAGTGACTTGGCAGAGGCATTGTAC

TTGGTCTGTGGTGAGAGAGGATTCTTCTACACCCCAAAGGAGTGGAAG

GGTATCGTTGAGCAATGTTGTACTTCCATCTGCTCA-XXX$_1$-XXX$_2$-C

AATTGGAGAACTACTGCAACTAA

SEQ ID NO: 24 provides the sense strand of a gene encoding a 53-residue single-chain insulin analogue with substitutions Asp$^{B10}$, Ala$^{B12}$ and Ala$^{B30}$ and with C-domain Ala-Lys such that the codon at position A13 (XXX$_1$) optionally encodes Leucine, Tyrosine or Trptophan, such that the codon at position A14 (XXX$_2$) optionally encodes Tyrosine or Glutamic Acid, and such that the first codon encodes Lysine.

SEQ ID NO: 24
AARGTCAATCAACACTTGTGTGGTAGTGACTTGGCAGAGGCTTTGTACTT

GGTCTGTGGTGAGAGAGGATTCTTCTACACCCCTAAGGCTGCTAAGGGAA

TCGTTGAGCAATGCTGTACTTCCATCTGCTCA-XXX$_1$-XXX$_2$-CAATTGGA

GAACTACTGCAACTAA

SEQ ID NO: 25 provides the sense strand of a gene encoding a 53-residue single-chain insulin analogue with substitutions Asp$^{B10}$, Ala$^{B12}$, Glu$^{48}$ and Glu$^{B30}$ and with C-domain Trp-Lys such that the codon at position A13 (XXX$_1$) optionally encodes Leucine, Tyrosine or Trptophan, such that the codon at position A14 (XXX$_2$) optionally encodes Tyrosine or Glutamic Acid, and such that the first codon encodes Lysine.

SEQ ID NO: 25
AARGTCAATCAACACTTGTGTGGTAGTGACTTGGCAGAGGCATTGTACTT

GGTCTGTGGTGAGAGAGGATTCTTCTACACCCCAAAGGAGTGGAAGGGTA

TCGTTGAGCAATGTTGTGAATCCATCTGCTCA-XXX$_1$-XXX$_2$-CAATTGGA

GAACTACTGCAACTAA

SEQ ID NO: 26 provides the sense strand of a gene encoding a 53-residue single-chain insulin analogue with substitution Asp$^{B10}$, Ala$^{B12}$, and Glu$^{B30}$ and with C-domain Trp-Lys such that a non-standard amino acid may be inserted through nonsense suppression at codon position B24 (TAG), such that the codon at position A13 (XXX$_1$) optionally encodes Leucine, Tyrosine or Trptophan, such that the codon at position A14 (XXX$_2$) optionally encodes Tyrosine or Glutamic Acid, and such that XXX$_3$ encodes Lysine.

SEQ ID NO: 26
AARGTCAATCAACACTTGTGTGGTAGTGACTTGGCAGAGGCATTGTACT

TGGTCTGTGGTGAGAGAGGATAGTTCTACACCCCAAAGGAGTGGAAGGG

TATCGTTGAGCAATGTTGTACTTCCATCTGCTCA-XXX$_1$-XXX$_2$-CAATT

GGAGAACTACTGCAACTAA

SEQ ID NO: 27 provides the sense strand of a gene encoding a 53-residue single-chain insulin analogue with substitution Glu$^{48}$, Ala$^{B12}$, Asp$^{B10}$ and Glu$^{B30}$ and with C-domain Trp-Lys such that a non-standard amino acid may be inserted through nonsense suppression at codon position B24 (TAG), such that the codon at position A13 (XXX$_1$) optionally encodes Leucine, Tyrosine or Trptophan, such the codon at position A14 (XXX$_2$) optionally encodes Tyrosine or Glutamic Acid, and such that the first codon encodes Lysine.

SEQ ID NO: 27
AARGTCAATCAACACTTGTGTGGTAGTGACTTGGCAGAGGCATTGTACT

TGGTCTGTGGTGAGAGAGGATAGTTCTACACCCCAAAGGAGTGGAAGGG

TATCGTTGAGCAATGTTGTGAATCCATCTGCTCA-XXX$_1$-XXX$_2$-CAATT

GGAGAACTACTGCAACTAA

SEQ ID NO: 28 provides the sense strand of a gene encoding a 53-residue single-chain insulin analogue with substitutions Asp$^{B10}$, Ala$^{B12}$, and Glu$^{B30}$, with C-domain Trp-Lys such that the codon at position A13 (XXX$_1$) optionally encodes Leucine, Tyrosine or Trptophan, such that the codon at position A14 (XXX$_2$) optionally encodes Tyrosine or Glutamic Acid, and such that the second codon encodes Lysine.

SEQ ID NO: 28
TTCAARAATCAACACTTGTGTGGTAGTGACTTGGCAGAGGCATTGTACT

TGGTCTGTGGTGAGAGAGGATTCTTCTACACCCCAAAGGAGTGGAAGGG

TATCGTTGAGCAATGTTGTACTTCCATCTGCTCA-XXX$_1$-XXX$_2$-CAATT

GGAGAACTACTGCAACTAA

SEQ ID NO: 29 provides the sense strand of a gene encoding a 53-residue single-chain insulin analogue with substitutions Asp$^{B10}$, Ala$^{B12}$, and Ala$^{B30}$ and with C-domain Ala-Lys such that the codon at position A13 (XXX$_1$) optionally encodes Leucine, Tyrosine or Trptophan, such that the codon at position A14 (XXX$_2$) optionally encodes Tyrosine or Glutamic Acid, and such that the second encodes Lysine.

SEQ ID NO: 29
TTCAARATCAACACTTGTGTGGTAGTGACTTGGCAGAGGCTTTGTACT

TGGTCTGTGGTGAGAGAGGATTCTTCTACACCCCTAAGGCTGCTAAGG

GAATCGTTGAGCAATGCTGTACTTCCATCTGCTCA-XXX$_1$-XXX$_2$-CAATT

GGAGAACTACTGCAACTAA

SEQ ID NO: 30 provides the sense strand of a gene encoding a 53-residue single-chain insulin analogue with substitutions Asp$^{B10}$, Ala$^{B12}$, Glu$^{48}$ and Glu$^{B30}$ and with C-domain Trp-Lys such that the codon at position A13 (XXX$_1$) optionally encodes Leucine, Tyrosine or Trptophan, such that the codon at position A14 (XXX$_2$) optionally encodes Tyrosine or Glutamic Acid, and such that the second codon encodes Lysine.

SEQ ID NO: 30
TTCAARAATCAACACTTGTGTGGTAGTGACTTGGCAGAGGCATTGTACT

TGGTCTGTGGTGAGAGAGGATTCTTCTACACCCCAAAGGAGTGGAAGGG

TATCGTTGAGCAATGTTGTGAATCCATCTGCTCA-XXX$_1$-XXX$_2$-CAATT

GGAGAACTACTGCAACTAA

SEQ ID NO: 31 provides the sense strand of a gene encoding a 53-residue single-chain insulin analogue with substitution Asp$^{B10}$, Ala$^{B12}$ and Glu$^{B30}$ and with C-domain Trp-Lys such that a non-standard amino acid may be inserted through nonsense suppression at codon position B24 (TAG), such that the codon at position A13 (XXX$_1$) optionally encodes Leucine, Tyrosine or Trptophan, such that the codon at position A14 (XXX$_2$) optionally encodes Tyrosine or Glutamic Acid, and such that the second codon encodes Lysine.

SEQ ID NO: 31
TTCAARAATCAACACTTGTGTGGTAGTGACTTGGCAGAGGCATTGTACT

TGGTCTGTGGTGAGAGAGGATAGTTCTACACCCCAAAGGAGTGGAAGGG

TATCGTTGAGCAATGTTGTACTTCCATCTGCTCA-XXX$_1$-XXX$_2$-CAATT

GGAGAACTACTGCAACTAA

SEQ ID NO: 32 provides the sense strand of a gene encoding a 53-residue single-chain insulin analogue with substitution Glu$^{A8}$, Asp$^{B10}$, Ala$^{B12}$, and Glu$^{B30}$ and with C-domain Trp-Lys such that a non-standard amino acid may be inserted through nonsense suppression at codon position B24 (TAG), such that the codon at position A13 (XXX$_1$) optionally encodes Leucine, Tyrosine or Trptophan, such the codon at position A14 (XXX$_2$) optionally encodes Tyrosine or Glutamic Acid, and such that the second codon encodes Lysine.

SEQ ID NO: 32
TTCAARAATCAACACTTGTGTGGTAGTGACTTGGCAGAGGCATTGTACT

TGGTCTGTGGTGAGAGAGGATAGTTCTACACCCCAAAGGAGTGGAAGGG

TATCGTTGAGCAATGTTGTGAATCCATCTGCTCA-XXX$_1$-XXX$_2$-CAATT

GGAGAACTACTGCAACTAA

SEQ ID NO: 33 provides the sense strand of a gene encoding a 53-residue single-chain insulin analogue with substitutions Asp$^{B10}$, Ala$^{B12}$ and Glu$^{B30}$, with C-domain Trp-Lys such that the codon at position A13 (XXX$_1$) optionally encodes Leucine, Tyrosine or Trptophan, such that the codon at position A14 (XXX$_2$) optionally encodes Tyrosine or Glutamic Acid, and such that the third codon encodes Lysine.

SEQ ID NO: 33
TTCGTCAARCAACACTTGTGTGGTAGTGACTTGGCAGAGGCATTGTACT

TGGTCTGTGGTGAGAGAGGATTCTTCTACACCCCAAAGGAGTGGAAGGG

TATCGTTGAGCAATGTTGTACTTCCATCTGCTCA-XXX$_1$-XXX$_2$-CAATT

GGAGAACTACTGCAACTAA

SEQ ID NO: 34 provides the sense strand of a gene encoding a 53-residue single-chain insulin analogue with substitutions Asp$^{B10}$, Ala$^{B12}$, and Ala$^{B30}$ and with C-domain Ala-Lys such that the codon at position A13 (XXX$_1$) optionally encodes Leucine, Tyrosine or Trptophan, such that the codon at position A14 (XXX$_2$) optionally encodes Tyrosine or Glutamic Acid, and such that the third codon encodes Lysine.

SEQ ID NO: 34
TTCGTCAARCAACACTTGTGTGGTAGTGACTTGGCAGAGGCTTTGTACT

TGGTCTGTGGTGAGAGAGGATTCTTCTACACCCCTAAGGCTGCTAAGGG

AATCGTTGAGCAATGCTGTACTTCCATCTGCTCA-XXX$_1$-XXX$_2$-CAATT

GGAGAACTACTGCAACTAA

SEQ ID NO: 35 provides the sense strand of a gene encoding a 53-residue single-chain insulin analogue with substitutions Asp$^{B10}$, Ala$^{B12}$, Glu$^{A8}$ and Glu$^{B30}$ and with C-domain Trp-Lys such that the codon at position A13 (XXX$_1$) optionally encodes Leucine, Tyrosine or Trptophan, such that the codon at position A14 (XXX$_2$) optionally encodes Tyrosine or Glutamic Acid, and such that the third codon encodes Lysine.

SEQ ID NO: 35
TTCGTCAARCAACACTTGTGTGGTAGTGACTTGGCAGAGGCATTGTACT

TGGTCTGTGGTGAGAGAGGATTCTTCTACACCCCAAAGGAGTGGAAGGG

TATCGTTGAGCAATGTTGTGAATCCATCTGCTCA-XXX$_1$-XXX$_2$-CAATT

GGAGAACTACTGCAACTAA

SEQ ID NO: 36 provides the sense strand of a gene encoding a 53-residue single-chain insulin analogue with substitution Asp$^{B10}$, Ala$^{B12}$, and Glu$^{B30}$ and with C-domain Trp-Lys such that a non-standard amino acid may be inserted through nonsense suppression at codon position B24 (TAG), such that the codon at position A13 (XXX$_1$) optionally encodes Leucine, Tyrosine or Trptophan, such that the codon at position A14 (XXX$_2$) optionally encodes Tyrosine or Glutamic Acid, and such that the third codon encodes Lysine.

SEQ ID NO: 36
TTCGTCAARCAACACTTGTGTGGTAGTGACTTGGCAGAGGCATTGTACT

TGGTCTGTGGTGAGAGAGGATAGTTCTACACCCCAAAGGAGTGGAAGGG

TATCGTTGAGCAATGTTGTACTTCCATCTGCTCA-XXX$_1$-XXX$_2$-CAATT

GGAGAACTACTGCAACTAA

SEQ ID NO: 37 provides the sense strand of a gene encoding a 53-residue single-chain insulin analogue with substitution Glu$^{A8}$, Asp$^{B10}$, Ala$^{B12}$ and Glu$^{B30}$ and with C-domain Trp-Lys such that a non-standard amino acid may be inserted through nonsense suppression at codon position B24 (TAG), such that the codon at position A13 (XXX$_1$) optionally encodes Leucine, Tyrosine or Trptophan, such the codon at position A14 (XXX$_2$) optionally encodes Tyrosine or Glutamic Acid, and such that the third codon encodes Lysine.

SEQ ID NO: 37
TTCGTCAARCAACACTTGTGTGGTAGTGACTTGGCAGAGGCATTGTACT

TGGTCTGTGGTGAGAGAGGATAGTTCTACACCCCAAAGGAGTGGAAGGG

TATCGTTGAGCAATGTTGTGAATCCATCTGCTCA-XXX$_1$-XXX$_2$-CAATT

GGAGAACTACTGCAACTAA

SEQ ID NOS: 13-37, providing DNA sequences, may be further modified in each case such that codon 29 (encoding Lys in the above sequences) instead encodes Glutamic Acid (codon GAG or GAA). These respective SEQ ID NOS: entries are designated 38-63. SEQ ID NO: 38 is related to SEQ ID NO: 13, SEQ ID NO: 39 is related to SEQ ID NO: 14, and so forth. For example, SEQ ID NO: 38 corresponding to SEQ ID NO: 13 is defined as follows:

SEQ ID NO: 38
TTCGTCAATCAACACTTGTGTGGTAGTGACTTGGCAGAGGCATTGTACTTG
GTCTGTGGTGAGAGAGGATTCTTCTACACCCCAGARGAGTGGAAGGGTATC
GTTGAGCAATGTTGTACTTCCATCTGCTCATTGTACCAATTGGAGAACTAC
TGCAACTAA

SEQ ID NO: 39
TTCGTCAATCAACACTTGTGTGGTAGTGACTTGGCAGAGGCTTTGTACTTG
GTCTGTGGTGAGAGAGGATTCTTCTACACCCCTGARGCTGCTAAGGGAATC
GTTGAGCAATGCTGTACTTCCATCTGCTCATTGTACCAATTGGAGAACTAC
TGCAACTAA

SEQ ID NO: 40
TTCGTCAATCAACACTTGTGTGGTAGTGACTTGGCAGAGGCATTGTACTTG
GTCTGTGGTGAGAGAGGATTCTTCTACACCCCAGARGAGTGGAAGGGTATC
GTTGAGCAATGTTGTGAATCCATCTGCTCATTGTACCAATTGGAGAACTAC
TGCAACTAA

SEQ ID NO: 41
TTCGTCAATCAACACTTGTGTGGTAGTGACTTGGCAGAGGCATTGTACTTG
GTCTGTGGTGAGAGAGGATAGTTCTACACCCCAGARGAGTGGAAGGGTATC
GTTGAGCAATGTTGTACTTCCATCTGCTCATTGTACCAATTGGAGAACTAC
TGCAACTAA

SEQ ID NO: 42
TTCGTCAATCAACACTTGTGTGGTAGTGACTTGGCAGAGGCATTGTACTT
GGTCTGTGGTGAGAGAGGATAGTTCTACACCCCAGARGAGTGGAAGGGTA
TCGTTGAGCAATGTTGTGAATCCATCTGCTCATTGTACCAATTGGAGAAC
TACTGCAACTAA

SEQ ID NO: 43
TTCGTCAATCAACACTTGTGTGGTAGTGACTTGGCAGAGGCATTGTACTT
GGTCTGTGGTGAGAGAGGATTCTTCTACACCCCAGARGAGTGGAAGGGTA
TCGTTGAGCAATGTTGTACTTCCATCTGCTCA-XXX1-XXX2-CAATTGG
AGAACTACTGCAACTAA
XXX1 is TTA, TTG, CTT, CTC, CTG, TAT, TAC, or TGG
XXX2 is TAT, TAC, GAA or GAG

SEQ ID NO: 44
TTCGTCAATCAACACTTGTGTGGTAGTGACTTGGCAGAGGCTTTGTACTT
GGTCTGTGGTGAGAGAGGATTCTTCTACACCCCTGARGCTGCTAAGGGAA
TCGTTGAGCAATGCTGTACTTCCATCTGCTCA-XXX1-XXX2-CAATTGG
AGAACTACTGCAACTAA
XXX1 is TTA, TTG, CTT, CTC, CTG, TAT, TAC, or TGG
XXX2 is TAT, TAC, GAA or GAG

SEQ ID NO: 45
TTCGTCAATCAACACTTGTGTGGTAGTGACTTGGCAGAGGCATTGTACT
TGGTCTGTGGTGAGAGAGGATTCTTCTACACCCCAGARGAGTGGAAGGG
TATCGTTGAGCAATGTTGTGAATCCATCTGCTCA-XXX1-XXX2-CAAT
TGGAGAACTACTGCAACTAA
XXX1 is TTA, TTG, CTT, CTC, CTG, TAT, TAC, or TGG
XXX2 is TAT, TAC, GAA or GAG

SEQ ID NO: 46
TTCGTCAATCAACACTTGTGTGGTAGTGACTTGGCAGAGGCATTGTACTT
GGTCTGTGGTGAGAGAGGATAGTTCTACACCCCAGARGAGTGGAAGGGTA
TCGTTGAGCAATGTTGTACTTCCATCTGCTCA-XXX1-XXX2-CAATTGG
AGAACTACTGCAACTAA
XXX1 is TTA, TTG, CTT, CTC, CTG, TAT, TAC, or TGG
XXX2 is TAT, TAC, GAA or GAG

SEQ ID NO: 47
TTCGTCAATCAACACTTGTGTGGTAGTGACTTGGCAGAGGCATTGTACTT
GGTCTGTGGTGAGAGAGGATAGTTCTACACCCCAGARGAGTGGAAGGGTA
TCGTTGAGCAATGTTGTGAATCCATCTGCTCA-XXX1-XXX2-
CAATTGGAGAACTACTGCAACTAA
XXX1 is TTA, TTG, CTT, CTC, CTG, TAT, TAC, or TGG
XXX2 is TAT, TAC, GAA or GAG

SEQ ID NO: 48
GARGTCAATCAACACTTGTGTGGTAGTGACTTGGCAGAGGCATTGTACTT
GGTCTGTGGTGAGAGAGGATTCTTCTACACCCCAAGARAGTGGAAGGGTA
TCGTTGAGCAATGTTGTACTTCCATCTGCTCA-XXX1-XXX2-
CAATTGGAGAACTACTGCAACTAA
XXX1 is TTA, TTG, CTT, CTC, CTG, TAT, TAC, or TGG
XXX2 is TAT, TAC, GAA or GAG

SEQ ID NO: 49
GARGTCAATCAACACTTGTGTGGTAGTGACTTGGCAGAGGCTTTGTACTT
GGTCTGTGGTGAGAGAGGATTCTTCTACACCCCTAGARCTGCTAAGGGAA
TCGTTGAGCAATGCTGTACTTCCATCTGCTCA-XXX1-XXX2-
CAATTGGAGAACTACTGCAACTAA
XXX1 is TTA, TTG, CTT, CTC, CTG, TAT, TAC, or TGG
XXX2 is TAT, TAC, GAA or GAG

SEQ ID NO: 50
GARGTCAATCAACACTTGTGTGGTAGTGACTTGGCAGAGGCATTGTAC
TTGGTCTGTGGTGAGAGAGGATTCTTCTACACCCCAAGARAGTGGAAG
GGTATCGTTGAGCAATGTTGTGAATCCATCTGCTCA-XXX1-XXX2-
CAATTGGAGAACTACTGCAACTAA
XXX1 is TTA, TTG, CTT, CTC, CTG, TAT, TAC, or TGG
XXX2 is TAT, TAC, GAA or GAG

SEQ ID NO: 51
GARGTCAATCAACACTTGTGTGGTAGTGACTTGGCAGAGGCATTGTAC
TTGGTCTGTGGTGAGAGAGGATAGTTCTACCCCCAAGARAGTGGAAGG
GTATCGTTGAGCAATGTTGTACTTCCATCTGCTCA-XXX1-XXX2-
CAATTGGAGAACTACTGCAACTAA

-continued

XXX1 is TTA, TTG, CTT, CTC, CTG, TAT, TAC, or TGG

XXX2 is TAT, TAC, GAA or GAG

SEQ ID NO: 52
GARGTCAATCAACACTTGTGTGGTAGTGACTTGGCAGAGGCATTGTA

CTTGGTCTGTGGTGAGAGAGGATTAGTTCTACCCCCAAGARAGTGGA

AGGGTATCGTTGAGCAATGTTGTGAATCCATCTGCTCA-XXX1-XXX2-

CAATTGGAGAACTACTGCAACTAA

XXX1 is TTA, TTG, CTT, CTC, CTG, TAT, TAC, or TGG

XXX2 is TAT, TAC, GAA or GAG

SEQ ID NO: 53
TTCGARAATCAACACTTGTGTGGTAGTGACTTGGCAGAGGCATTGTA

CTTGGTCTGTGGTGAGAGAGGATTCTTCTACACCCCAAGARAGTGGA

AGGGTATCGTTGAGCAATGTTGTACTTCCATCTGCTCA-XXX1-XXX2-

CAATTGGAGAACTACTGCAACTAA

XXX1 is TTA, TTG, CTT, CTC, CTG, TAT, TAC, or TGG

XXX2 is TAT, TAC, GAA or GAG

SEQ ID NO: 54
TTCGARAATCAACACTTGTGTGGTAGTGACTTGGCAGAGGCTTTGTAC

TTGGTCTGTGGTGAGAGAGGATTCTTCTACACCCCTAGARCTGCTAAG

GGAATCGTTGAGCAATGCTGTACTTCCATCTGCTCA-XXX1-XXX2-

CAATTGGAGAACTACTGCAACTAA

XXX1 is TTA, TTG, CTT, CTC, CTG, TAT, TAC, or TGG

XXX2 is TAT, TAC, GAA or GAG

SEQ ID NO: 55
TTCGARAATCAACACTTGTGTGGTAGTGACTTGGCAGAGGCATTGTA

CTTGGTCTGTGGTGAGAGAGGATTCTTCTACACCCCAAGARAGTGGA

AGGGTATCGTTGAGCAATGTTGTGAATCCATCTGCTCA-XXX1-XXX2-

CAATTGGAGAACTACTGCAACTAA

XXX1 is TTA, TTG, CTT, CTC, CTG, TAT, TAC, or TGG

XXX2 is TAT, TAC, GAA or GAG

SEQ ID NO: 56
TTCGARAATCAACACTTGTGTGGTAGTGACTTGGCAGAGGCATTGTAC

TTGGTCTGTGGTGAGAGAGGATAGTTCTACACCCCAAGARAGTGGAAG

GGTATCGTTGAGCAATGTTGTACTTCCATCTGCTCA-XXX1-XXX2-

CAATTGGAGAACTACTGCAACTAA

XXX1 is TTA, TTG, CTT, CTC, CTG, TAT, TAC, or TGG

XXX2 is TAT, TAC, GAA or GAG

SEQ ID NO: 57
TTCGARAATCAACACTTGTGTGGTAGTGACTTGGCAGAGGCATTGTA

CTTGGTCTGTGGTGAGAGAGGATAGTTCTACACCCCAAGARAGTGGA

AGGGTATCGTTGAGCAATGTTGTGAATCCATCTGCTCA-XXX1-XXX2-

CAATTGGAGAACTACTGCAACTAA

XXX1 is TTA, TTG, CTT, CTC, CTG, TAT, TAC, or TGG

XXX2 is TAT, TAC, GAA or GAG

SEQ ID NO: 58
TTCGTCGARCAACACTTGTGTGGTAGTGACTTGGCAGAGGCATTGTA

CTTGGTCTGTGGTGAGAGAGGATTCTTCTACACCCCAGARGAGTGGA

AGGGTATCGTTGAGCAATGTTGTACTTCCATCTGCTCA-XXX1-XXX2-

CAATTGGAGAACTACTGCAACTAA

XXX1 is Leu, Tyr or Trp TTA, TTG, CTT, CTC, CTG, TAT, TAC, or TGG

XXX2 is Tyr or Glu TAT, TAC, GAA or GAG

SEQ ID NO: 59
TTCGTCGARCAACACTTGTGTGGTAGTGACTTGGCAGAGGCTTTGTAC

TTGGTCTGTGGTGAGAGAGGATTCTTCTACACCCCTGARCTGCTAAG

GGAATCGTTGAGCAATGCTGTACTTCCATCTGCTCA-XXX1-XXX2-

CAATTGGAGAACTACTGCAACTAA

XXX1 is Leu, Tyr or Trp TTA, TTG, CTT, CTC, CTG, TAT, TAC, or TGG

XXX2 is Tyr or Glu TAT, TAC, GAA or GAG

SEQ ID NO: 60
TTCGTCGARCAACACTTGTGTGGTAGTGACTTGGCAGAGGCATTGTAC

TTGGTCTGTGGTGAGAGAGGATTCTTCTACACCCCAGARGAGTGGAAG

GGTATCGTTGAGCAATGTTGTGAATCCATCTGCTCA-XXX1-XXX2-

CAATTGGAGAACTACTGCAACTAA

XXX1 is Leu, Tyr or Trp TTA, TTG, CTT, CTC, CTG, TAT, TAC, or TGG

XXX2 is Tyr or Glu TAT, TAC, GAA or GAG

SEQ ID NO: 61
TTCGTCGARCAACACTTGTGTGGTAGTGACTTGGCAGAGGCATTGTAC

TTGGTCTGTGGTGAGAGAGGATAGTTCTACACCCCAGARGAGTGGAAG

GGTATCGTTGAGCAATGTTGTACTTCCATCTGCTCA-XXX1-XXX2-

CAATTGGAGAACTACTGCAACTAA

XXX1 is Leu, Tyr or Trp TTA, TTG, CTT, CTC, CTG, TAT, TAC, or TGG

XXX2 is Tyr or Glu TAT, TAC, GAA or GAG

SEQ ID NO: 62
TTCGTCGARCAACACTTGTGTGGTAGTGACTTGGCAGAGGCATTGTAC

TTGGTCTGTGGTGAGAGAGGATAGTTCTACACCCCAGARGAGTGGAAG

GGTATCGTTGAGCAATGTTGTGAATCCATCTGCTCA-XXX1-XXX2-

CAATTGGAGAACTACTGCAACTAA

XXX1 is Leu, Tyr or Trp TTA, TTG, CTT, CTC, CTG, TAT, TAC, or TGG

XXX2 is Tyr or Glu TAT, TAC, GAA or GAG

The rationale for these two related sets of DNA sequences is that Glutamic Acid at position B29 may be introduced into an insulin analogue via semi-synthesis employing a synthetic C-terminal B-chain peptide containing Glutamic acid at final position B29 or may be introduced directly into the single-chain biosynthetic precursor.

Two single-chain insulin analogues of the present invention were prepared by biosynthesis of a precursor polypeptide in *Pichia pastoris*; this system secretes a folded protein containing native disulfide bridges with cleavage N-terminal extension peptide. Tryptic cleavage of this precursor protein yields a two-chain insulin fragment containing a truncated B chain beginning at residue Phe$^{B1}$ and ending at Arg$^{B22}$ and a complete A chain. The precursor polypeptides are encoded by synthetic genes whose sequences are given in SEQ ID NOS: 13-64, which in each case contain the substitution Asp$^{B10}$ and Ala$^{B12}$, and may optionally contain the additional substitutions Glu$^{48}$, Glu$^{B29}$, and/or Glu$^{414}$. Single-chain insulin precursors are also envisaged containing a nonsense codon at position B24 such that non-standard amino-acid substitutions may be inserted via an engineered orthogonal tRNA synthetase; such precursors would not be processed by trypsin but instead split by a lysine-specific endopeptidase.

Figure 3:
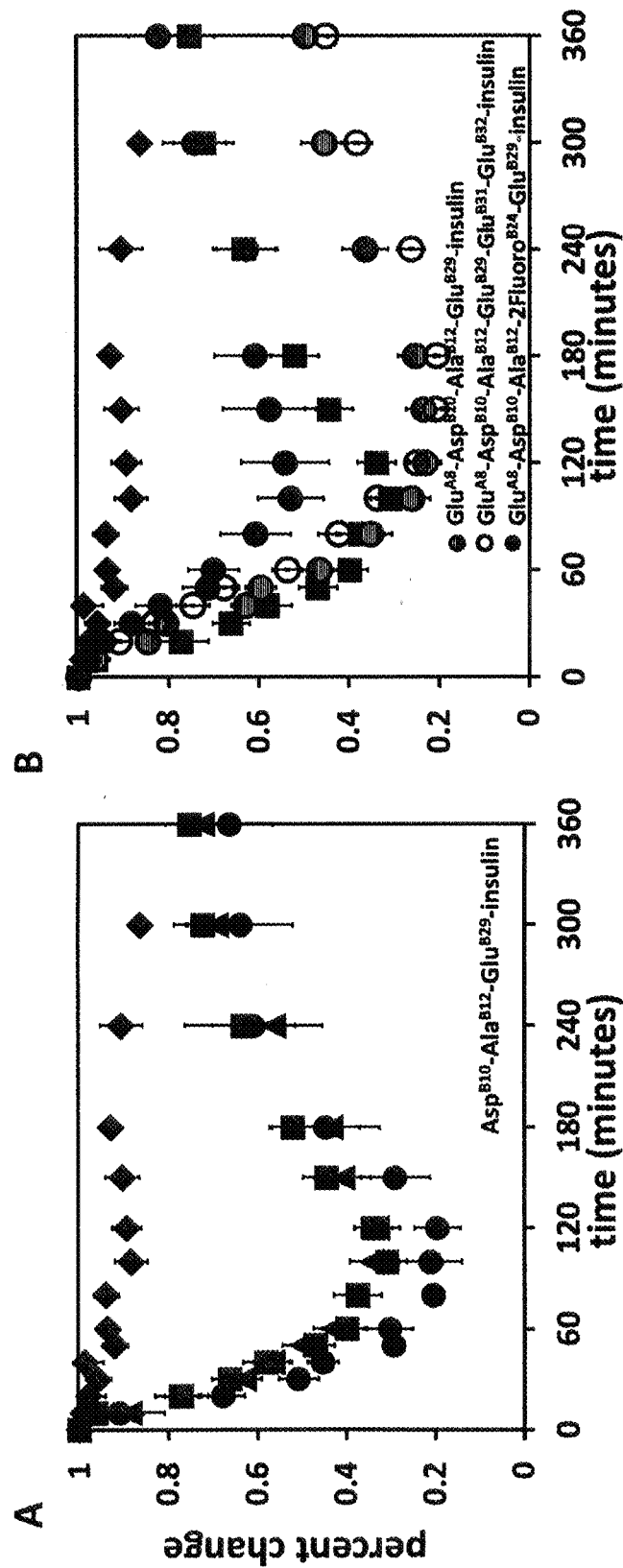
FIG. 3 provides a pair of graphs showing the pharmacodynamics response of diabetic Sprague-Dawley rats to the subcutaneous injection of insulin analogues.

Biological activity and pharmacodynamics were tested in male Sprague-Dawley rats (ca. 300 g) rendered diabetic by streptozotocin (FIG. 3). FIG. 3 provides an assay of the pharmacodynamics response of diabetic Sprague-Dawley rats to the subcutaneous injection of insulin analogues. At time 0 min, the rats (with mean baseline blood-glucose concentration 400±20 mg/dl) were injected s.q. with 1 unit of the indicated insulin analog/300 g body weight. (A) The following were injected subcutaneously: (♦) diluent control, (■) Humalog (insulin lispro), (▲) Asp$^{B10}$, Ala$^{B12}$, Glu$^{B29}$-insulin (T-0334), and (●) Asp$^{B10}$ derivative of insulin lispro ("DKP-insulin"). (B) The following were injected subcutaneously: (♦) diluent control, (■) Humalog (insulin lispro), (⊛) Glu$^{48}$, Asp$^{B10}$, Ala$^{B12}$, Glu$^{B29}$-insulin (T-0181), (0) Glu$^{B31}$, Glu$^{B32}$-extended version of Glu$^{48}$, Asp$^{B10}$, Ala$^{B12}$, Glu$^{B29}$-insulin (T-0182), and (●) 2F-Phe$^{B24}$ derivative of Glu$^{48}$, Asp$^{B10}$, Ala$^{B12}$, Glu$^{B29}$-insulin (T-0184). Error bars, standard errors. PD effects of s.q. injection of four representative insulin analogues, each containing the core three substitutions (Asp$^{B10}$, Ala$^{B12}$ and Glu$^{B29}$ in the presence or absence of other optional design elements), were evaluated in relation to Humalog® and an Asp$^{B10}$ derivative of insulin lispro (DKP-insulin); the resulting overall profile of the blood-glucose concentration (FIG. 3) indicated that the PD properties of our two candidates are similar to that of Humalog®. The receptor-binding affinities of the insulin analogues were determined in relation to wild-type human insulin (data not shown). Values were observed in the range 5-100% relative to wild-type human insulin in studies of the lectin-purified and detergent solubilized insulin receptor (isoforms A and B). Dissociation constants ($K_d$) were determined by fitting to a mathematic model as described by Whittaker and Whittaker (2005. *J. Biol. Chem.* 280: 20932-20936); the model employed non-linear regression with the assumption of heterologous competition (Wang, 1995, *FEBS Lett.* 360: 111-114).

Figure 4:
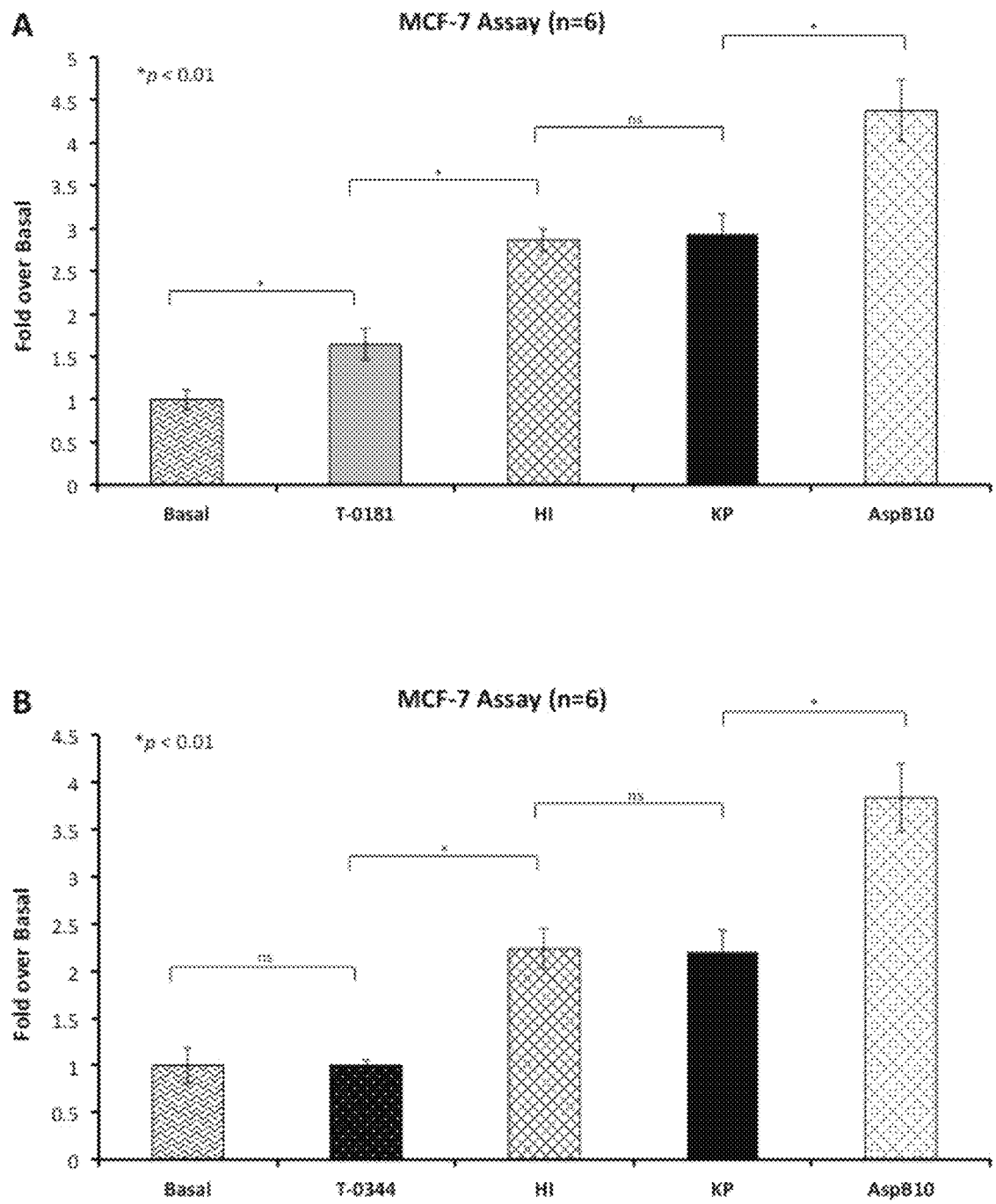
FIG. 4 provides a pair of histograms showing the results of an assay of the mitogenicity of insulin analogues as assessed in studies of MCF-7 human breast cancer cells grown in soft agar.

Assay for MCF-7 Colony Formation in Soft Agar. Single-cell suspensions were obtained by mixing a 0.75-ml suspension (~1.5×10$^3$ cells) of MCF-7 cells with 0.75 ml of pre-warmed (42° C.) 0.6% Bacto-Agar suspension. This 0.3% suspension was poured onto a 1.5-ml layer of 0.6% agar in 12-well plates. The agar was overlaid with growth medium (without insulin supplemented) ±10 nM of the insulin analogues and re-fed 3×/week for 3 weeks. Colonies (>100 μm) were counted on day 21. Results are shown in FIG. 4. Tests of Asp$^{B10}$, Ala$^{B12}$, Glu$^{B29}$-insulin (T-0334) and of Glu$^{48}$, Asp$^{B10}$, Ala$^{B12}$, Glu$^{B29}$-insulin (T-0181) revealed a reduction in mitogenicity relative to wild-type human insulin (labeled "HI" in FIG. 4), insulin lispro ("KP"), or Asp$^{B10}$-insulin ("AspB10"; far right). In these assays statistical significance was obtained the level of p-values less than 0.05.

Figure 5:
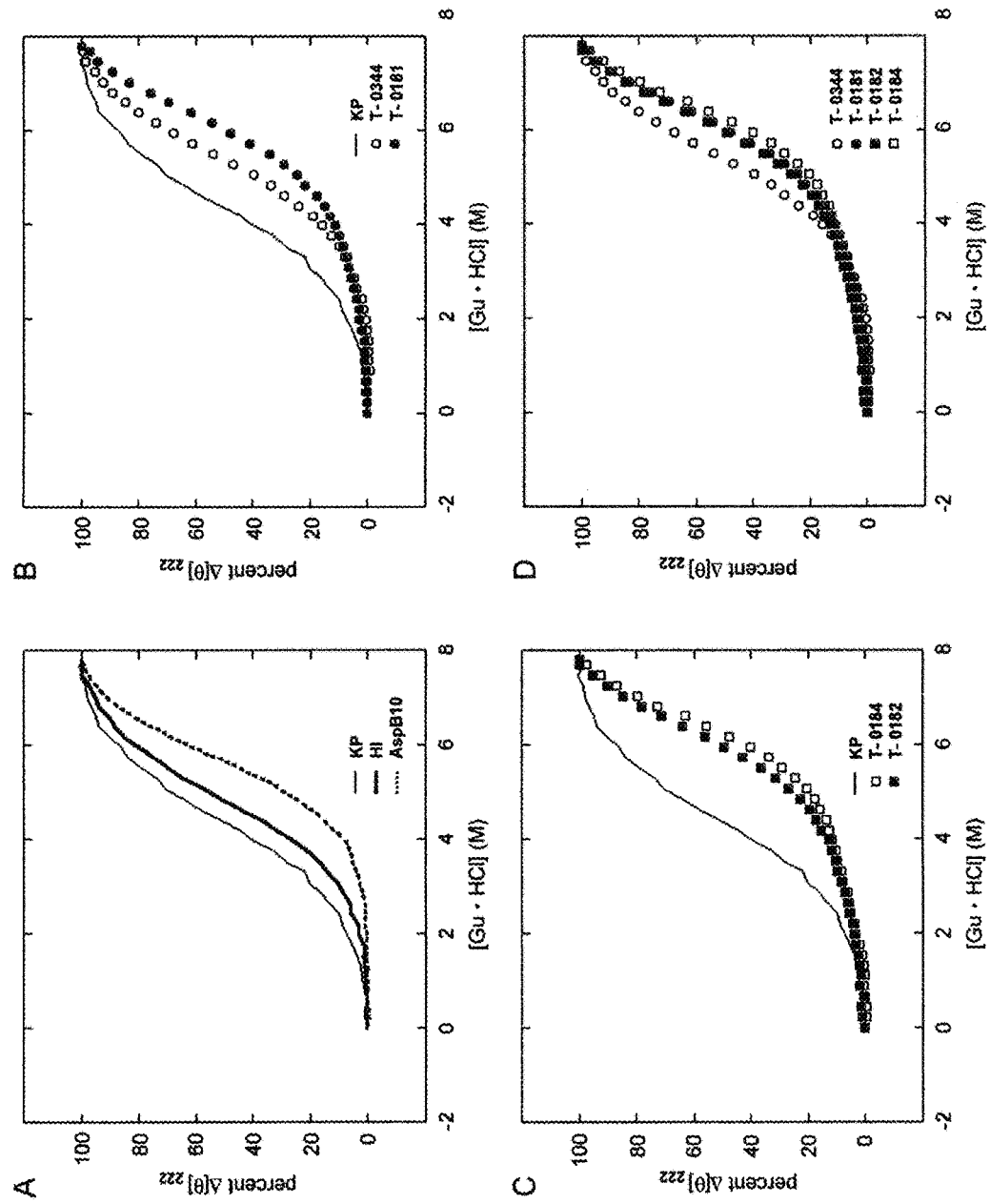
FIG. 5 provides a series of graphs of assays of thermodynamic stability as probed by chemical denaturation at 25° C. with CD-detected ellipticity at a helix-sensitive wavelength (222 nm) shown on the vertical axis as a function of the concentration of guanidine hydrochloride.

The thermodynamic stabilities of the insulin analogues were probed by CD-monitored guanidine denaturation as shown in FIG. 5. The method was as described (Hua, Q. X., et al. *J. Biol. Chem.* 283, 14703-16 (2008)). The results indicate that these analogues are each as stable or more stable to chemical denaturation than are wild-type insulin or KP-insulin (respective free energies of unfolding ($\Delta G_u$) at 25° C. 3.4±0.1 and 2.9±0.1 kcal/mole; see FIG. 6 and Table 1 below). The estimates of $\Delta G_u$ at 25° C. provided in Table 1 were obtained by application of an analogous two-state model extrapolated to zero denaturant concentration: (analogue T-0334) 3.6±0.1 kcal/mole, (analogue T-0181) 4.6±0.1 kcal/mole, (analogue T-0182) 4.9±0.1 kcal/mole, (analog T-0184) 5.8±0.2 kcal/mole. Such higher values of $\Delta G_u$ predict enhanced resistance of the present insulin analogues to chemical degradation under zinc-free conditions than would be observed in studies of wild-type insulin or KP-insulin under the same conditions.

FIG. 4 provides an assay of the mitogenicity of insulin analogues as assessed in studies of MCF-7 human breast cancer cells grown in soft agar. (A) Comparison of Glu$^{48}$, Asp$^{B10}$, Ala$^{B12}$, Glu$^{B29}$-insulin (T-0181) with human insulin (labeled "HI"), insulin lispro ("KP"), Asp$^{B10}$-insulin ("AspB10"; far right) and insulin-free medium along ("basal"; far left). (B) Comparison of Asp$^{B10}$, Ala$^{B12}$, Glu$^{B29}$-insulin (T-0334) with the same control set. Brackets and asterisks indicate p-values less than 0.05 as a metric of statistical significance; numbers of replicates (N) are as specified.

FIG. 5 provides assays of thermodynamic stability as probed by chemical denaturation at 25° C. In these assays CD-detected ellipticity at a helix-sensitive wavelength (222 nm) is shown on the vertical axis as a function of the concentration of guanidine hydrochloride. Free energies of unfolding at zero denaturant concentration ($\Delta G_u$; see Table 1) were inferred by application of a two-state model. (A) Control studies of wild-type human insulin (labeled "HI"; thick solid line), insulin lispro ("KP"; thin solid line), and Asp$^{B10}$, Orn$^{B29}$-human insulin (dotted line). (B) Comparative studies of Asp$^{B10}$, Ala$^{B12}$, Glu$^{B29}$-insulin (T-0334) and the Glu$^{48}$ derivative of Asp$^{B10}$, Ala$^{B12}$, Glu$^{B29}$-insulin (T-0181) versus insulin lispro (KP; thin solid line). (C) Comparative studies of the Glu$^{B31}$, Glu$^{B32}$-extended version of Glu$^{48}$, Asp$^{B10}$, Ala$^{B12}$, Glu$^{B29}$-insulin (T-0182) and the 2F-Phe$^{B24}$ derivative of Glu$^{48}$, Asp$^{B10}$, Ala$^{B12}$, Glu$^{B29}$-insulin (T-0184) versus insulin lispro (KP; thin solid line). (D) Comparative studies of the four insulin analogues containing the core three substitutions of the present invention: Asp$^{B10}$, Ala$^{B12}$, and Glu$^{B29}$.

Figure 6:
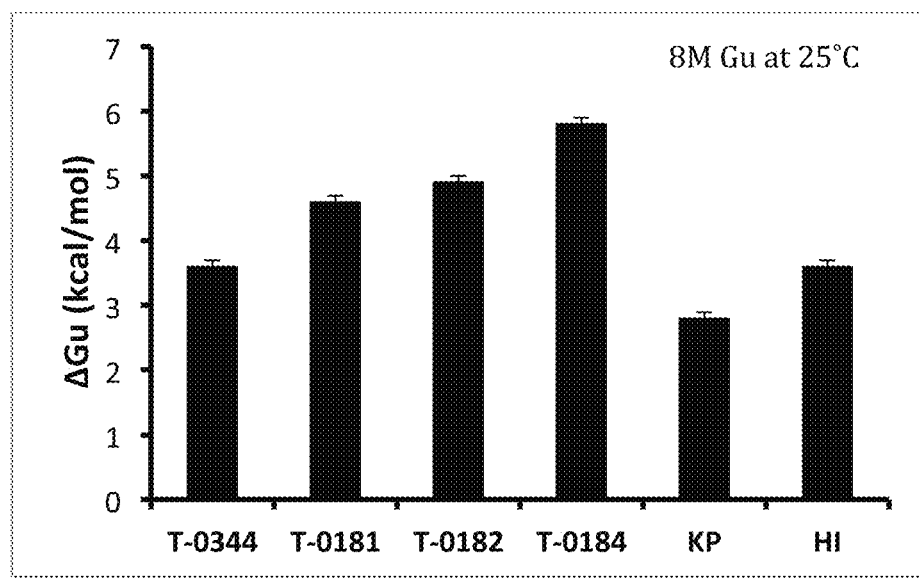
FIG. 6 is a histogram in which the thermodynamic stabilities of insulin analogues are indicated by height of the bars. T-numbers refer to the following analogs: (T-0334) $Asp^{B10}$, $Ala^{B12}$, $Glu^{B29}$-insulin, (T-0181) $Glu^{A8}$ derivative of $Asp^{B10}$, $Ala^{B12}$, $Glu^{B29}$-insulin, (T-0182) $Glu^{B31}$, $Glu^{B32}$-extended version of $Glu^{A8}$, $Asp^{B10}$, $Ala^{B12}$, $Glu^{B29}$-insulin, and (T-0184) 2F-$Phe^{B24}$ derivative of $Glu^{A8}$, $Asp^{B10}$, $Ala^{B12}$, $Glu^{B29}$-insulin. "HI" indicates wild-type human insulin, and "KP" designates insulin lispro.

FIG. 6 provides a histogram in which the thermodynamic stabilities of insulin analogues are indicated by height of the bars (see also Table 1). T-numbers refer to the following analogs: (T-0334) Asp$^{B10}$, Ala$^{B12}$, Glu$^{B29}$-insulin, (T-0181) Glu$^{48}$ derivative of Asp$^{B10}$, Ala$^{B12}$, Glu$^{B29}$-insulin, (T-0182) Glu$^{B31}$, Glu$^{B32}$-extended version of Glu$^{48}$, Asp$^{B10}$, Ala$^{B12}$, Glu$^{B29}$-insulin, and (T-0184) 2F-Phe$^{B24}$ derivative of Glu$^{48}$, Asp$^{B10}$, Ala$^{B12}$, Glu$^{B29}$-insulin. "HI" indicates wild-type human insulin, and "KP" designates insulin lispro.

A method for treating a patient with diabetes mellitus comprises administering a two-chain insulin analogue as described herein. It is another aspect of the present invention that the two-chain insulin analogues may be prepared either in yeast (*Pichia pastoris*) or subject to total chemical synthesis by native fragment ligation. The synthetic route of preparation is preferred in the case of non-standard modifications, such as D-amino-acid substitutions, halogen substitutions within the aromatic rings of Phe or Tyr, or O-linked modifications of Serine or Threonine by carbohydrates; however, it would be feasible to manufacture a subset of the single-chain analogues containing non-standard modifications by means of extended genetic-code technology or four-base codon technology (for review, see Hohsaka, T., & Sisido, M., 2012). It is yet another aspect of the present invention that use of non-standard amino-acid substitutions can augment the resistance of the two-chain insulin analogue to chemical degradation or to physical degradation. We further envision the analogues of the present invention providing a method for the treatment of diabetes mellitus or the metabolic syndrome. The route of delivery of the insulin analogue is by subcutaneous injection through the use of a syringe or pen device. An insulin analogue of the present invention may also contain other modifications, such as a halogen atom at position B24. An insulin analogue of the present invention may also contain a foreshortened B-chain due to deletion of residues B1-B3.

A pharmaceutical composition may comprise such insulin analogues and which may optionally include zinc. Because the insulin analogues of the present invention do not form classical zinc-stabilized hexamers (and indeed do not require such assembly for stability), zinc ions may be included at varying zinc ion:protein ratios lower than are typically employed in formulations containing a predominance of insulin hexamers; such ratios may be in the range 0.01-0.10 moles of zinc ions per mole of insulin analogue. The pH of the formulation is in the range pH 7.0-8.0; a buffer (typically sodium phosphate or Tris-hydrochloride) may or may not be present. In such a formulation, the concentration of the insulin analogue would typically be between about 0.6-5.0 mM; concentrations up to 5 mM may be used in vial or pen; the more concentrated formulations (U-200 or higher) may be of particular benefit in patients with marked insulin resistance. Excipients may include glycerol, glycine, arginine, Tris, other buffers and salts, and anti-microbial preservatives such as phenol and meta-cresol; the latter preservatives are known to enhance the stability of the insulin hexamer. Such a pharmaceutical composition may be used to treat a patient having diabetes mellitus or other medical condition by administering a physiologically effective amount of the composition to the patient.

Based upon the foregoing disclosure, it should now be apparent that the two-chain insulin analogues provided will carry out the objects set forth hereinabove. Namely, these insulin analogues exhibit biological activity (as defined by the nanomoles of protein monomer required to lower the blood-glucose concentration in a mammal on subcutaneous or intravenous injection) similar to that of wild-type insulin such that rapid action is retained with reduced mitogenicity. It is, therefore, to be understood that any variations evident fall within the scope of the claimed invention and thus, the selection of specific component elements can be determined without departing from the spirit of the invention herein disclosed and described.

TABLE 1

Thermodynamic Stabilities[a] (pH 7.4 and 25° C.)

| analog | $\Delta G_u^b$ (kcal/mol) | $C_{mid}^c$ (M) | $m^d$ (kcal/mol/M) |
|---|---|---|---|
| KP-insulin (lispro) | 2.9 ± 0.1 | 4.6 ± 0.2 | 0.65 ± 0.03 |
| Human insulin (HI) | 3.4 ± 0.1 | 4.9 ± 0.1 | 0.69 ± 0.02 |
| Asp$^{B10}$, Orn$^{B29}$-insulin | 4.6 ± 0.1 | 5.8 ± 0.1 | 0.60 ± 0.02 |
| T-0344 | 3.6 ± 0.1 | 5.8 ± 0.2 | 0.62 ± 0.02 |
| T-0181 | 4.6 ± 0.1 | 6.4 ± 0.2 | 0.72 ± 0.02 |
| T-0182 | 4.9 ± 0.1 | 6.7 ± 0.2 | 0.73 ± 0.02 |
| T-0184 | 5.8 ± 0.2 | 6.8 ± 0.2 | 0.87 ± 0.03 |

[a]Thermodynamic stabilities were inferred from CD-detected guanidine denaturation studies at 25° C. by application of a two-state model.
[b]$\Delta G_u$ indicates apparent change in free energy on denaturation in guanidine-HCL as extrapolated to zero-denaturant concentration
[c]$C_{mid}$ is defined as the concentration of guanidine-HCL at which 50% of the protein is unfolded.
[d]The m value provides the slope in plotting unfolding free energy $\Delta G_u$ versus molar concentration of denaturant; this slope is proportional to the protein surface area exposed on unfolding.

The following literature is cited to demonstrate that the testing and assay methods described herein would be understood by one of ordinary skill in the art.

Barnes-Seeman, D., Beck, J., and Springer, C. (2014) Fluorinated compounds in medicinal chemistry: recent applications, synthetic advances and matched-pair analyses. *Curr. Top. Med. Chem.* 14:855-64.

Brange J, editor. (1987) *Galenics of Insulin: The Physicochemical and Pharmaceutical Aspects of Insulin and Insulin Preparations*. Berlin: Springer Berlin Heidelberg.

Hohsaka, T., and Sisido, M. (2012) Incorporation of non-natural amino acids into proteins. *Curr. Opin. Chem. Biol.* 6, 809-15.

Kalra, S., Balhara, Y., Sahay, B., Ganapathy, B., and Das, A. (2013) Why is premixed insulin the preferred insulin? Novel answers to a decade-old question. *J. Assoc. Physicians India* 61, 9-11.

Liu, M., Hua, Q. X., Hu, S. Q., Jia, W., Yang, Y., Saith, S. E., Whittaker, J., Arvan, P., and Weiss, M. A. (2010) Deciphering the hidden informational content of protein sequences: foldability of proinsulin hinges on a flexible arm that is dispensable in the mature hormone. *J. Biol. Chem.* 285:30989-1001.

Voloshchuk, N., Zhu, A. Y., Snydacker D., and Montclare, J. K. (2009) Positional effects of monofluorinated phenylalanines on histone acetyltransferase stability and activity. *Bioorg. Med. Chem. Lett.* 19:5449-51.

Vølund, A., Brange, J., Drejer, K., Jensen, I., Markussen, J., Ribel, U., Sorensen, A. R., and Schlichtkrull, J. (1991) In vitro and in vivo potency of insulin analogues designed for clinical use. *Diabet. Med.* 8:839-47.

Wang, Z. X. (1995) An exact mathematical expression for describing competitive binding of two different ligands to a protein molecule *FEBS Lett.* 360: 111-114.

Whittaker, J., and Whittaker, L. (2005) Characterization of the functional insulin binding epitopes of the full-length insulin receptor. *J. Biol. Chem.* 280: 20932-20936.

Yang, Y., Petkova, A., Huang, K., Xu, B., Hua, Q. X., Ye, I. J., Chu, Y. C., Hu, S. Q., Phillips, N. B., Whittaker, J., Ismail-Beigi, F., Mackin, R. B., Katsoyannis, P. G., Tycko, R., and Weiss, M. A. (2010) An Achilles' heel in an amyloidogenic protein and its repair: insulin fibrillation and therapeutic design. *J. Biol. Chem.* 285:10806-21.

Yuvienco, C., More, H. T., Haghpanah, J. S., Tu, R. S., and Montclare, J. K. (2012) Modulating supramolecular assemblies and mechanical properties of engineered protein materials by fluorinated amino acids. *Biomacromolecules* 13:2273-8.

What is claimed is:

1. A polypeptide comprising an insulin B-chain amino acid sequence containing the substitutions Asp at position B10, Ala at position B12, and Glu at position B29, relative to the amino acid sequence of wild type human insulin.

2. The polypeptide according to claim 1, wherein the B-chain amino acid sequence comprises SEQ ID NO: 5.

3. The polypeptide according to claim 1, wherein the B-chain amino acid sequence comprises SEQ ID NO: 6.

4. The polypeptide according to claim 1, additionally comprising a substitution of a halogenated phenylalanine at position B24, relative to the amino acid sequence of wild type insulin.

5. The polypeptide according to claim 4, wherein the halogenated phenylalanine is ortho-fluoro-phenylalanine.

6. The polypeptide of claim 5 wherein the B-chain amino acid sequence comprises SEQ ID NO: 9.

7. The polypeptide according to claim 1, wherein the B-chain amino acid sequence additionally comprises a C-terminal dipeptide extension wherein at least one amino acid in the dipeptide contains an acidic side chain.

8. The polypeptide of claim 7, wherein the C-terminal dipeptide extension is Glu-Glu.

9. The polypeptide of claim 8, wherein the B-chain amino acid sequence comprises SEQ ID NO: 8.

10. An insulin analogue comprising a polypeptide according to claim 1 and additionally comprising an insulin A-chain polypeptide.

11. The insulin analogue of claim 10 wherein the insulin A-chain polypeptide comprises a Glu substitution at position A8, relative to the sequence of wild type insulin.

12. The insulin analogue of claim 11 wherein the insulin A-chain polypeptide comprises SEQ ID NO: 7.

13. The insulin analogue of claim 11 wherein the insulin A-chain polypeptide additionally comprises a substitution at position A13 relative to the sequence of wild type insulin selected from the group consisting of Leu, Tyr and Trp and a substitution at position A14 relative to the sequence of wild type insulin selected from the group consisting of Tyr and Glu.

14. The insulin analogue of claim 11, wherein the A-chain polypeptide sequence is connected to the B-chain polypeptide by disulfide bridges between positions A6-A11, A7-B7, and A20-B19.

15. The insulin analogue of claim 11, wherein the insulin analogue is a single chain insulin analogue, wherein the B-chain and A-chain polypeptide sequences are connected by a dipeptide linker between the C-terminal end of the B-chain and the N-terminal end of the A-chain.

16. The insulin analogue of claim 15, wherein the dipeptide linker is selected from Trp-Lys and Ala-Lys.

17. A method of lowering the blood sugar of a patient, the method comprising administering a physiologically effective amount of an insulin analogue comprising an insulin B-chain sequence that comprises an amino acid sequence that contains the substitutions Asp at position B10, Ala at position B12, and Glu at position B29, relative to the amino acid sequence of wild type human insulin.

18. The method of claim 17, wherein the insulin analogue additionally comprises an insulin A-chain polypeptide which comprises a Leu, Tyr or Trp substitution at position A13 relative to the sequence of wild type insulin and a Tyr or Glu substitution at position A14 relative to the sequence of wild type insulin.

* * * * *